United States Patent
Rutkove et al.

(10) Patent No.: US 9,974,463 B2
(45) Date of Patent: May 22, 2018

(54) HAND-HELD DEVICE FOR ELECTRICAL IMPEDANCE MYOGRAPHY

(75) Inventors: Seward B. Rutkove, Brookline, MA (US); Joel L. Dawson, Roslindale, MA (US)

(73) Assignees: Beth Israel Deaconess Medical Center, Inc., Boston, MA (US); Massachusetts Institute of Technology, Cambridge, MA (US)

( * ) Notice: Subject to any disclaimer, the term of this patent is extended or adjusted under 35 U.S.C. 154(b) by 995 days.

(21) Appl. No.: 13/391,484

(22) PCT Filed: Aug. 20, 2010

(86) PCT No.: PCT/US2010/002295
§ 371 (c)(1),
(2), (4) Date: Jun. 6, 2012

(87) PCT Pub. No.: WO2011/022068
PCT Pub. Date: Feb. 24, 2011

(65) Prior Publication Data
US 2012/0245436 A1    Sep. 27, 2012

Related U.S. Application Data
(60) Provisional application No. 61/236,009, filed on Aug. 21, 2009.

(51) Int. Cl.
*A61B 5/053* (2006.01)
*A61B 5/00* (2006.01)

(52) U.S. Cl.
CPC ............ *A61B 5/053* (2013.01); *A61B 5/4519* (2013.01); *A61B 5/6843* (2013.01); *A61B 5/0536* (2013.01);
(Continued)

(58) Field of Classification Search
CPC ... A61B 5/0536; A61B 5/0488; A61B 5/0492; A61B 5/053; A61B 2562/046; A61B 2562/0209; A61B 2018/124
(Continued)

(56) References Cited

U.S. PATENT DOCUMENTS 6,122,544 A * 9/2000 Organ .......................... 600/547
2003/0028092 A1   2/2003 Anderson et al.
(Continued)

FOREIGN PATENT DOCUMENTS

EP         1 275 342 A2       1/2003
WO      WO 02/056766 A1       7/2002
(Continued)

OTHER PUBLICATIONS

International Search Report dated Sep. 30, 2010 from corresponding International Application No. PCT/US2010/002295.
(Continued)

*Primary Examiner* — Adam J Eiseman
(74) *Attorney, Agent, or Firm* — Wolf, Greenfield & Sacks, P.C.

(57) ABSTRACT

A device for determining muscle condition of a region of tissue. The device comprises an electrical impedance myography (EIM) portable probe bearing an electrode array. The electrode array comprises excitation electrodes used to apply multi-frequency electrical signals to the region of tissue and pickup electrodes that are used to collect electrical signals resulting from the application of the multi-frequency electrical signals to the region of tissue. To improve accuracy and reproducibility of EIM measurements, the electrode array is reconfigurable to select different subsets of excitation and pickup electrodes so that the electrodes are oriented differently with respect to muscle fibers. Additional devices may be associated with the EIM probe to measure such
(Continued)

parameters as temperature, moisture content of the region, quality of contact of electrodes of the electrode array with a surface of the region and pressure with which the EEM probe is applied to the region. The EIM measurements may be adjusted based on these parameters. Also, ultrasound and electrical impedance tomography measurements may supplement the ELM measurements for more complete analysis of the muscle condition.

10 Claims, 34 Drawing Sheets

(52) U.S. Cl.
CPC ..... *A61B 5/0537* (2013.01); *A61B 2560/0252* (2013.01); *A61B 2560/0276* (2013.01); *A61B 2562/0209* (2013.01); *A61B 2562/046* (2013.01)

(58) Field of Classification Search
USPC .................................................. 600/546, 547
See application file for complete search history.

(56) References Cited

U.S. PATENT DOCUMENTS

| 2003/0130711 | A1* | 7/2003 | Pearson ............. A61B 18/1477 607/101 |
| 2004/0019292 | A1* | 1/2004 | Drinan .................. A61B 5/053 600/547 |
| 2006/0085049 | A1* | 4/2006 | Cory et al. ....................... 607/48 |
| 2010/0076328 | A1 | 3/2010 | Matsumura et al. |

FOREIGN PATENT DOCUMENTS

| WO | WO 2007035887 A2 * | 3/2007 | ........... A61B 5/0488 |
| WO | WO 2007041783 A1 | 4/2007 | |
| WO | WO 2007053963 A1 | 5/2007 | |
| WO | WO 2008065873 A1 | 6/2008 | |

OTHER PUBLICATIONS

International Preliminary Report on Patentability for Application No. PCT/US2010/002295 dated Mar. 1, 2012.

* cited by examiner

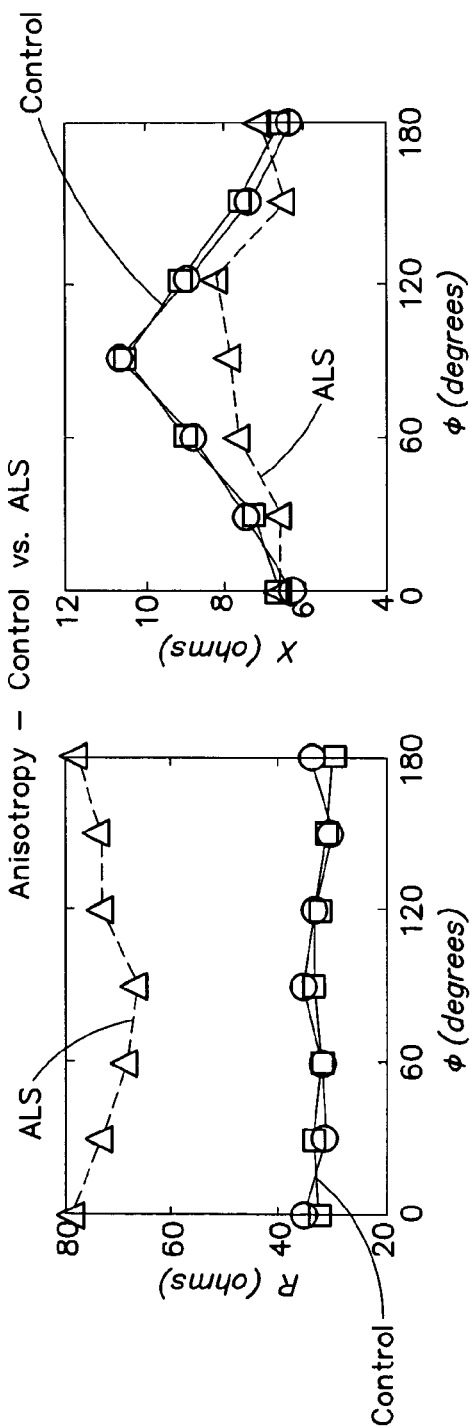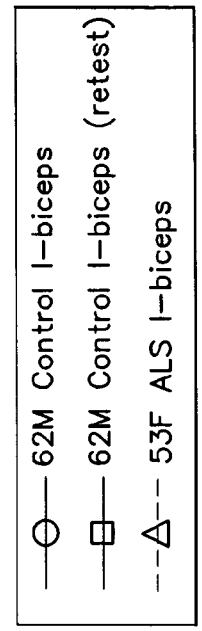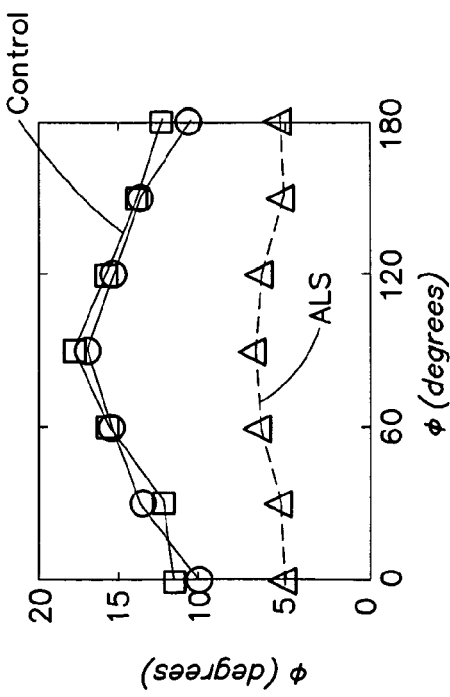
FIG. 8B
FIG. 8A
FIG. 8C

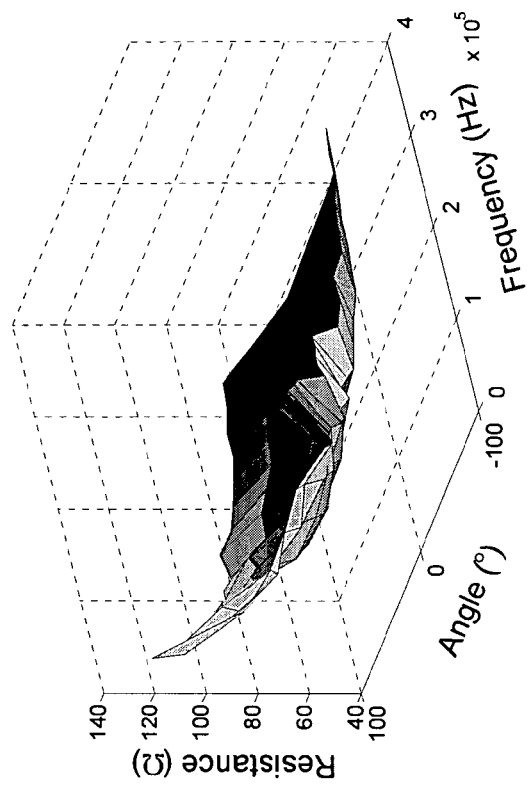
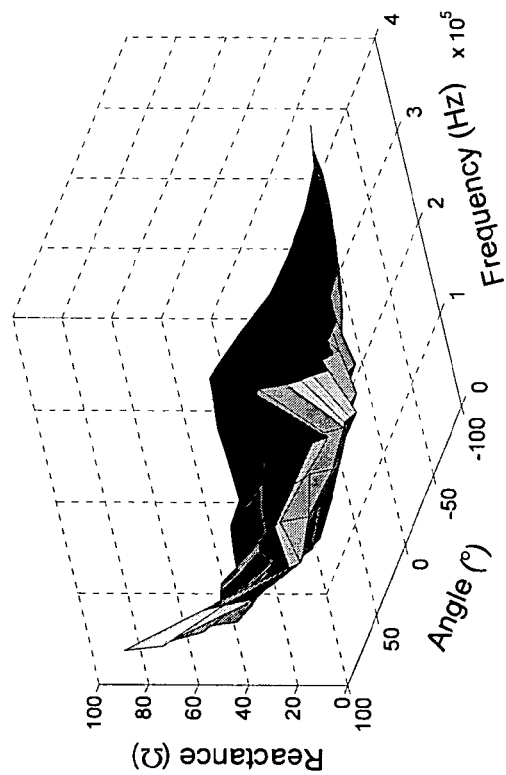
FIG. 26

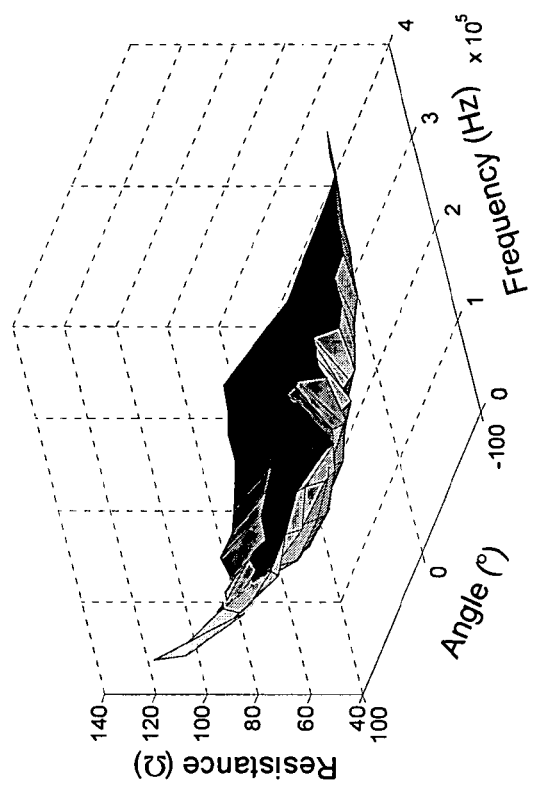
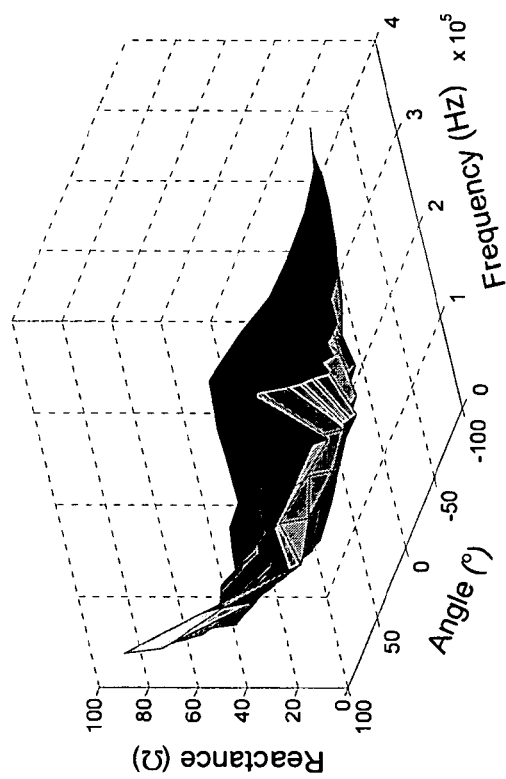
FIG. 27

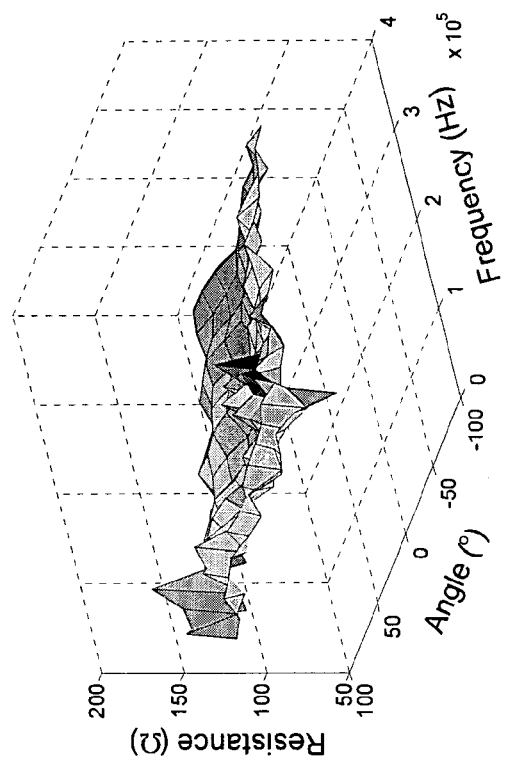
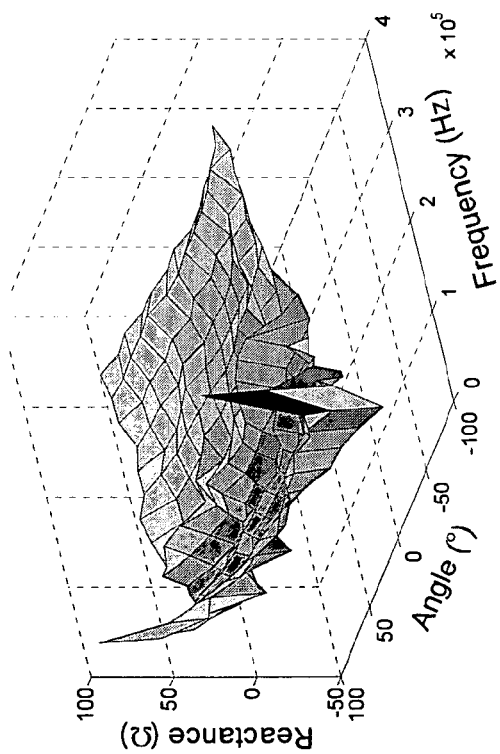
FIG. 28

HAND-HELD DEVICE FOR ELECTRICAL IMPEDANCE MYOGRAPHY

RELATED APPLICATION

This application claims priority under 35 U.S.C. § 119(e) to U.S. Provisional Application Ser. No. 61/236,009, entitled "A HAND-HELD DEVICE FOR ELECTRICAL IMPEDANCE MYOGRAPHY," filed on Aug. 21, 2009, which is herein incorporated by reference in its entirety.

FEDERALLY SPONSORED RESEARCH

This invention was made with government support under grant NS042037 awarded by NIH and W81XWH-07-2-0011 awarded by the Department of Defense. The government has certain rights in the invention.

BACKGROUND

Neuromuscular diseases encompass a large collection of disorders, ranging from relatively mild conditions such as focal compression neuropathies and nerve root injuries (e.g., a carpal tunnel syndrome), to severe and life-threatening syndromes, including amyotrophic lateral sclerosis (ALS) and muscular dystrophies. These disorders may lead to muscle atrophy and weakness, caused either by injury to or disease of the neuron (neurogenic disorders), the neuromuscular junction, or the muscle cell itself (myopathic disorders). Another disorder, disuse atrophy, that may occur when a limb is immobilized or a patient is bed-bound for a prolonged period of time, although not classically considered a neuromuscular disorder, also produces substantial morbidity.

Neuromuscular diseases have been assessed and diagnosed using various techniques, including nerve condition studies, needle electromyography, muscle imaging, muscle biopsy and genetic testing. However, the initial assessment of the neuromuscular diseases has advanced relatively little beyond conventional needle electromyography and nerve conduction techniques. Similarly, there have been few good approaches to the assessment of disuse atrophy and dysfunction.

Nerve conduction studies (NCSs) and needle electromyography (EMG) are often the first tests obtained when evaluating a patient for neuromuscular causes of atrophy. NCSs involve stimulation of a nerve with one set of electrodes and recording the resulting muscle or nerve potential with a second set of electrodes. Although useful for evaluating nerve pathology, NCSs are of limited use for evaluating muscle disease or disuse states. The stimuli can be uncomfortable and only a relatively limited set of distal muscles in the arms and legs can be evaluated.

Needle electromyography is geared more specifically to muscle evaluation. Needle electromyography can provide a quick survey of muscles to determine whether they are being affected by neurogenic injury or myopathic injury. However, the test has considerable limitations. First, needle electromyography is very subjective because physicians qualitatively assess the attributes of motor unit action potentials (MUAPs) as they rapidly pass across an oscilloscopic display. Second, there are substantial limitations with respect to the sensitivity of needle electromyography. It is a common experience amongst electromyographers that only with extensive probing are one or two questionably abnormal MUAPs identified. Third, the lack of quantifiable results makes EMG an unsuitable modality for following disease progression/remission. Finally, needle EMG remains a somewhat painful, invasive procedure and can thus only be used in a very limited fashion in children.

Imaging techniques such as magnetic resonance imaging (MRI) and ultrasound have found some use in muscle atrophy assessment. For example, MRI can be used to identify muscles with active inflammation to assist with biopsy site choice in patients with myositis. However, MRI has otherwise remained of limited use since it is difficult to evaluate different areas of the body, is costly, cannot easily assess dynamic muscle states during muscle contraction, and may not be used in patients with pacemakers and implanted defibrillators. Ultrasound has found limited use in neuromuscular disease and disuse atrophy assessment, and remains very qualitative.

Muscle biopsy is another test for evaluation of muscle disease and can be helpful in arriving at a specific diagnosis. Muscle biopsy frequently yields limited or contradictory information and may be unsuitable for monitoring progression of atrophy because of its inherent invasiveness. Given that many diseases are patchy (i.e., regions of diseased muscle tissue is interspersed throughout ostensibly healthy muscle tissue), a negative biopsy does not exclude disease, and repeat biopsies sometimes need to be performed.

Genetic tests can be very useful for assisting in the evaluation of a number of mostly rare conditions (such as the muscular dystrophies), but is expensive and not relevant to a variety of the most common, acquired conditions.

SUMMARY

Existing techniques for assessing and diagnosing neuromuscular diseases can be unreliable, subjective and sometimes painful to the patient. Embodiments of the invention relate to methods and devices that can provide a reliable, quantitative and relatively painless assessment and diagnoses of neuromuscular diseases, and for assessment of disuse atrophy. Applicants have developed generally non-invasive techniques for characterizing muscle tissue, facilitating the assessment, diagnosis, monitoring and/or treatment of characteristics and/or conditions of muscle tissue that may be indicative of one or more neuromuscular disorders, including disuse atrophy.

Embodiments of the invention relate to methods and devices for determining a characteristic of a region of tissue by applying an electrical signal to the region and, in response to applying the electrical signal, obtaining an electrical measurement of the region of tissue. Such a technique may be referred to as electrical impedance myography (EIM).

One embodiment according to the present invention includes a method of determining at least one characteristic of a region of tissue, the method comprising acts of applying a plurality of first electrical signals to the region of tissue, each of the plurality of first electrical signals being applied at a respective one of a plurality of orientations, obtaining a plurality of measurements from the region of tissue, each of the plurality of measurements indicative of a respective one of a plurality of second electrical signals, each of the plurality of second electrical signals resulting from applying a respective one of the plurality of first electrical signals, and determining the at least one characteristic based, at least in part, on the plurality of measurements.

Another embodiment according to the present invention includes a method of determining at least one characteristic of a region of tissue, the method comprising acts of applying a plurality of first electrical signals to the region of tissue, each of the plurality of first electrical signals being applied at a respective one of a plurality of frequencies, obtaining a plurality of measurements from the region of tissue, each of the plurality of measurements indicative of a respective one of a plurality of second electrical signals, each of the plurality of second electrical signals resulting from applying a respective one of the plurality of first electrical signals, and determining the at least one characteristic based, at least in part, on the plurality of measurements.

Another embodiment according to the present invention includes a device adapted for application to a surface of skin to determine at least one characteristic of a region of tissue, the device comprising a first electrode adapted to apply a first electrical signal to the region of tissue, a second electrode adapted to detect a second electrical signal at the region of tissue resulting from the application of the first electrical signal, a rotatable base on which the first electrode and the second electrode are mounted and arranged such that, when the rotatable base is rotated, the first electrode and the second electrode are rotated with respect to the region of tissue to apply the first electrical signal to the region of tissue at a plurality of orientations and to detect the second electrical signal resulting from the application of the first electrical signal at the plurality of orientations, and a measurement component coupled to the second electrode to obtain at least one measurement indicative of the second electrical signal at each of the plurality of orientations.

Some embodiments according to the present invention are premised on an observation that muscle conducts electrical current preferentially along a direction of its fibers rather than across its fibers. Thus, measurement of angular anisotropy in muscle may assist in assessing muscle health and in disease diagnosis. Thus, some embodiments according to the present invention provide a system and a device that simplify measurements of the angular anisotropy in muscle tissue. The ELM measurement system may comprise various components. The device may be a hand-held device, also referred to as a probe, which allows obtaining impedance or other measurements of patient's muscle tissues faster and easier. In the probe, electrodes may be located on a part referred to as a head of the probe.

In some embodiments, the head of the probe may be of a shape that allows to perform measurements on a patient in a more convenient and efficient matter. For example, the shape of the head of the probe may conform to a curve and shape of a limb or another part of the body. The head of the probe may therefore comprise any suitable curvatures that make the use of the probe more efficient since a closer contact with the scanned surface may be achieved and different areas of the patent's body may be scanned faster and with an improved precision. The probe may comprise a head of a fixed shape, meaning that the head is manufactured to have a permanent shape. Also, the head of the shape may be flexible (via any suitable mechanisms such as spring, etc.) so that the head may conform to the curvature of a scanned surface during application of the probe.

In some embodiments, the device may employ an array of electrodes designed to allow the device to take impedance measurements at multiple orientations with respect to muscle fibers. Operation of the electrode array may utilize a principle of the linearity of muscle tissue to reduce a required measurement time. The array of electrodes may be located at a head of a probe. In the array, neighboring electrodes may be electrically connected together so that the electrodes may act as a single unit. The array may be of any suitable configuration and arrangement. For example, the array may comprise multiple concentric or otherwise oriented rings. Also, a rectangular electrode array or an array comprising a combination of ring(s) and rows may be employed. Any other suitable configurations of the electrodes may be used as well. Furthermore, the electrodes may comprise vias, pins, solder pads or other suitable electrode elements.

The array of the electrodes may be positioned on a head of probe in any suitable manner. When a shape of the head is designed to conform to a curve and a shape of a limb or another part of the body, the array of the electrodes may be positioned on the head in a manner that allows to obtain measurements efficiently and accurately.

In the EIM measurement system, the electrode array may be reconfigurable such that the electrodes may be oriented differently with respect to muscle fibers which may reduce a time required to obtain measurements. Applying the electrodes at multiple angles relative to the orientation of muscle fibers may allow obtaining more complete measurements. Also, accuracy and reproducibility of results may be improved because the orientation of the electrodes with respect to the muscle fibers may be altered without physical movement of a head of the probe that bears the electrodes.

Furthermore, the device may be used to apply a signal comprising multiple tones which allows measurements of impedance or other parameters at multiple frequencies simultaneously. This may reduce a time required to obtain the measurements. The simultaneous measurement of impedance at multiple frequencies using a reconfigurable electrode array may ensure that EIM measurements are robust, rapidly obtained, and reliable.

In some embodiments, a method of determining at least one first characteristic of a region of tissue is provided. The method comprises selecting at least one first subset of a first plurality of electrodes to apply a first electrical signal comprising a plurality of frequencies to the region of tissue, detecting at least one value of at least one second characteristic of the region of tissue during a time when the first electrical signal is applied to the region of tissue, selecting at least one second subset of a second plurality of electrodes to detect a second electrical signal at the region of tissue resulting from the application of the first subset, wherein the first plurality of electrodes is reconfigurable to select at least one third subset of the first plurality of electrodes to apply the first electrical signal to the region of tissue and the second plurality of electrodes is reconfigurable to select at least one fourth subset of the second plurality of electrode to detect the second electrical signal at the region of tissue resulting from the application of the third subset, and adjusting the second electrical signal based on the at least one value of the at least one second characteristic.

In some embodiments, a device for determining muscle condition of a region of tissue is provided. The device may comprise a portable probe which comprises a body, a plurality of electrodes mounted on a base, and at least one sensor. The plurality of electrodes comprise at least one first subset of a first plurality of electrodes adapted to apply a first electrical signal comprising a plurality of frequencies to the region of tissue, and at least one second subset of a second plurality of electrodes to detect a second electrical signal at the region of tissue resulting from the application of the first subset, wherein the first plurality of electrodes is reconfigurable to select at least one third subset of the first plurality of electrodes to apply the first electrical signal to the region of tissue and the second plurality of electrodes is reconfigurable to select at least one fourth subset of the second plurality of electrode to detect the second electrical signal at the region of tissue resulting from the application of the third subset. The portable probe also comprises the at least one sensor that is adapted to obtain at least one first value of at least one characteristic of the region of tissue during a time when the first electrical signal is applied to the region of tissue.

The EIM probe in accordance with some embodiments of the invention may comprise any suitable devices that may improve efficiency of the probe and accuracy of impedance measurements. Thus, in some embodiments, the probe may comprise a temperature sensor that allows measuring temperature of a surface of the patient's skin when the probe is applied to the patient's body. Measuring the temperature of the patient's skin may be used to account for variations in the impedance measurements obtained when the probe is applied to the surface of the skin having different temperature. Other suitable devices may be, for example, one or more pressure sensors detecting a pressure with which the EIM probe is applied to the skin of a region of tissue, a moisture sensor to determine moisture content of the skin, an ultrasound sensor, an electrical tomography sensor and any other sensors. The sensor may be incorporated at a head of the EIM probe or otherwise associated with the probe.

The foregoing is a non-limiting summary of the invention, which is defined by the attached claims.

BRIEF DESCRIPTION OF THE DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings:

FIGS. 8A-C show plots of measured electrical parameters versus angular orientation of the measurement obtained in accordance with various aspects of the invention;

FIG. 26 illustrates impedance plots showing current conduction properties of human muscle tissue of a normal subject;

FIG. 27 illustrates impedance plots showing current conduction properties of human muscle tissue of a patient with amyotrophic lateral sclerosis (ALS);

FIG. 28 illustrates impedance plots showing current conduction properties of human muscle tissue of a patient with inclusion body myositis;

DETAILED DESCRIPTION

Figure 1:
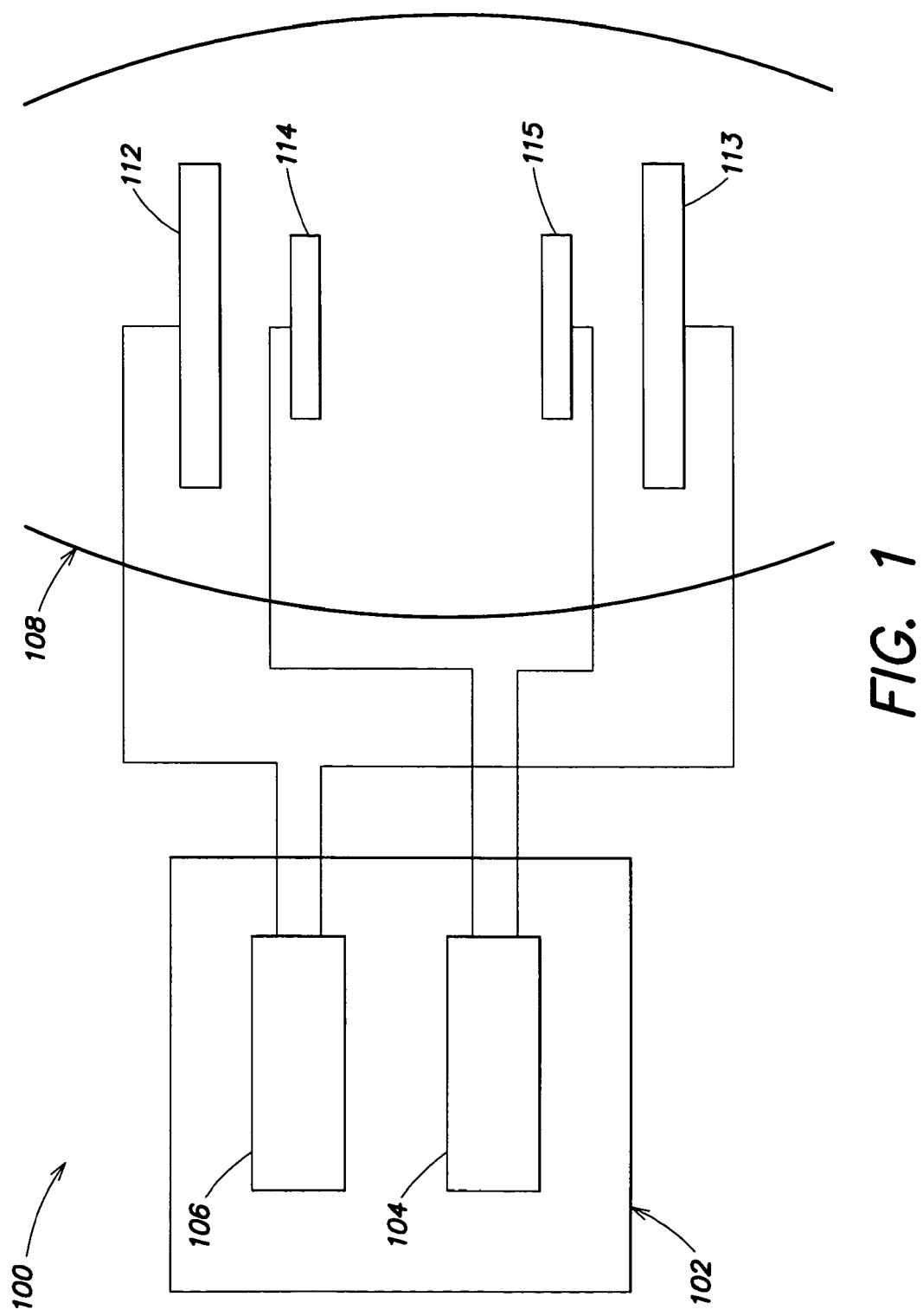
FIG. 1 is a diagram illustrating an example of a device that performs electrical impedance myography, according to one embodiment of the invention.

Embodiments of the invention relate to methods and devices for electrical impedance myography (EIM). Neuromuscular disorders can be assessed and diagnosed based on the measured electrical signals. In some embodiments, the quantitative nature of the techniques described herein can facilitate the evaluation of the progress of a neuromuscular disorder. For example, the effectiveness of treatments for neuromuscular disorders, such as newly-developed drugs, may be evaluated using the techniques described herein.

To perform an EIM technique, an electrical signal (e.g., electric current) may be applied to the region of tissue using electrodes applied to the skin. Various characteristics can be determined based on the electrical parameters that are measured for the region, such as the impedance, reactance, resistance and/or phase shift. In contrast to existing techniques for assessing and diagnosing neuromuscular disease, EIM may be more rapid, more quantitative, less invasive and more repeatable. EIM can be used for the assessment of muscle conditions, and more specifically, neuromuscular disease. However, it should be appreciated that EIM is not limited to the assessment of neuromuscular disease, as any other suitable tissue characteristic(s) may be measured using EIM, such as the amount of muscle atrophy that has occurred through disuse of a muscle (or more rarely, hypertrophy), as the aspects of the invention are not limited in this respect.

Some embodiments of the invention relate to methods and devices for performing multi-frequency EIM, which involves performing DM using at least two different frequencies of electrical signals. Because the electrical parameters of a muscle can be dependent on the frequency of an alternating current applied to a muscle, measurements of the muscle impedance for a plurality of frequencies can be utilized to facilitate diagnosis of muscle condition, and to differentiate between normal and abnormal muscle tissue. Multi-frequency EMI can be performed by varying the frequency of the alternating current applied to the muscle or group of muscles. For example, the frequency that is applied may be in the range between about 2 kHz and about 2 MHz, but the invention is not limited to this particular frequency range, as any other suitable frequency range can be used.

In addition to employing sequential application of signals of different frequencies, a multi-frequency signal may be used to achieve rapid data acquisition at multiple frequencies simultaneously. Thus, in some embodiments of the invention, the multi-frequency signal may be used. The applied signal may be, for example, of frequencies between 10 kHz and 4 MHz. However, it should be appreciated that the invention is not limited to this particular frequency range, as any other suitable frequency range can be used. Thus, in some embodiments, the applied signal may be of a frequency lower than 10 kHz. Signals of frequencies higher than 4 MHz may also be applied.

The alternating current can be injected via one set of surface electrodes (referred to as current-injecting electrodes), and the resulting voltage patterns can be recorded via a second set of surface electrodes (referred to as voltage-recording electrodes). Based on the measurement of the injected current's magnitude, an impedance instrument can convert the voltage signals into a resistance (R) and reactance (X), for each applied frequency. From these parameters, a phase (A) may be computed, for each applied frequency. However, any suitable electrical parameters may be measured and/or calculated for evaluation of muscle tissue, as the invention is not limited in this respect.

The current-injecting and voltage-recording electrode may form an array of electrodes that may be configured to adopt different configurations at which the array operates as a single composite electrode. In some embodiments, each set of the electrodes may be arranged into a ring, with different sets of electrodes forming multiple concentric ring configurations. Any suitable number of rings, as well as other geometric configurations, may be used in the electrode array as embodiments of the invention are not limited in this respect.

In some embodiments, excitation electrodes may be selected from electrode elements that form an outer ring, while pickup electrodes may be selected from electrode elements that form two inner rings. Though, any other suitable combinations of electrodes may be implemented. Thus, in some embodiments, additional electrodes may be utilized, which may improve reproducibility of the impedance measurements.

As an example, additional excitation and pickup electrodes may be employed to evaluate a depth of a skin-subcutaneous fat layer, which may be used to account for effects of impedance at different depths of this layer on the impedance measurements of the muscle tissue. In such situations, rings (formed of multiple electrodes) with smaller radii (e.g., the innermost rings of a plurality of concentric rings) may be used to analyze areas with smaller depths of the skin-subcutaneous fat layer. Rings with larger radii (e.g., the outermost rings of the plurality of concentric rings that include the innermost rings with the smaller radii) may be used to analyze areas with larger depths of the skin-subcutaneous fat layer.

Furthermore, in some embodiments, changes in muscle condition (e.g., a progression of a disease) along a certain direction in the muscle tissue may be detected using different sets of excitation and pickup electrodes. As such, impedance measurements obtained using one set of electrodes (e.g., forming the outermost rings) may be compared to impedance measurements obtained using other set of electrodes (e.g., forming the innermost rings). Other suitable combinations of the sets of electrodes may also be utilized.

In some embodiments, in the electrode array of the ELM probe, functions of the excitation and pickup electrodes may be interchangeable. In other words, each of the individual electrodes or a group of electrodes may be programmed to operate as either excitation or pickup electrodes.

Some embodiments of the invention relate to a method and apparatus for performing multidirectional EIM (also referred to as rotational EIM). Because the measured electrical parameters of a muscle can be anisotropic, and therefore dependent on the orientation of the measurement electrodes relative to the muscle fibers, electrical parameter measurements in a plurality of different directions can be utilized to facilitate diagnosis of muscle condition, and to differentiate between normal and abnormal muscle tissue.

In some embodiments of the invention, a method and apparatus is provided for both multi-frequency and multi-directional EIM. Such combined measurements can provide more diagnostic information than multi-frequency or multidirectional EIM alone. In some embodiments, a method and apparatus is provided for performing EIM during contraction of a muscle, referred to as dynamic ELM. The contraction can be voluntary or electrically induced.

In some embodiments, the EIM probe may be used to obtain impedance measurements during alternating contraction and relaxation of the underlying muscle or muscle group(s). In such scenarios, any suitable combination of contraction and relaxation of the muscles may be employed. Changes in impedance measurements with contraction of the muscles may provide useful data that may be indicative of neuromuscular abnormalities of the muscles. Such data may thus be used to differentiate between normal and diseased and to identify a type of a disease. In some embodiments, the ELM probe may be supplemented with a suitable device (e.g., a force transducer) to measure the muscle contraction. Hence, simultaneous measurements of impedance and contraction force of the muscle may be obtained. In some embodiments, during obtaining such simultaneous measurements, electrical nerve stimulation may be implemented to assess various properties of the muscle.

In yet other embodiments, a combination of multi-frequency, multidirectional, and/or dynamic EIM measurements can also be used to differentiate between different types of abnormal muscle conditions, including neuromuscular conditions (e.g., amyotrophic lateral sclerosis (ALS), inflammatory myopathy) and neurogenic conditions. A stage of a disease may be assessed as well. It should be appreciated that any of the aforementioned embodiments can be performed on one or more muscles including quadriceps, biceps, tibialis anterior, etc., as the invention is not limited to any specific muscle or muscle group.

In some embodiments of the invention, a method and apparatus are provided for use of a composite signal comprising multiple tones that makes possible measurements of impedance of muscle tissue at multiple frequencies simultaneously. This may reduce a time required to obtain the measurements.

Furthermore, an EIM measurement system may be provided that allows taking impedance measurements at multiple orientations with respect to muscle fibers by using an electrode array which may be reconfigurable. In some embodiments of the invention, such system may comprise a portable probe with a head bearing an electrode array having electrodes elements arranged in any suitable manner. The electrode array may be reconfigurable (e.g., electronically) such that the electrodes may be oriented differently with respect to muscle fibers which may reduce a time required to obtain measurements. More complete measurements may be obtained by applying the electrodes at multiple angles relative to the orientation of muscle fibers. Moreover, accuracy, speed and reproducibility of results may be improved because the orientation of the electrodes with respect to the muscle fibers may be altered without physical movement of the head of the probe.

In some embodiments of the invention, simultaneous measurement of impedance at multiple frequencies using a reconfigurable electrode array may ensure that EIM measurements are robust, rapidly obtained, and reliable. The user-friendliness and convenience of use of the portable device for EIM measurements makes it an attractive tool for use in various settings. For example, the patient may not need to be moved to conduct measurements because the device may be brought to a location of the patient, which may be particularly useful for diagnosing and monitoring neuromuscular diseases in bedridden patients.

In some embodiments, the EIM measurement system may allow, in addition to obtaining impedance measurements, to obtain measurements of different additional parameters to thus improve efficiency of the system and increase accuracy of assessment and/or diagnosis of a muscle condition. These additional measurements may be collected as part of monitoring of different factors that may affect the quality of the impedance measurements. Accordingly, the EIM system may comprise one or more suitable devices (e.g., suitable sensors) to obtain the measurements of the additional parameters. The devices may be associated with an EIM probe in any suitable manner. For example, one or more devices may be incorporated in a suitable location at a head of the EIM probe.

The additional parameters may provide information on the patient's skin conditions, quality of EIM measurements being obtained and other factors. Thus, the additional devices may be used to obtain measurements of such parameters as, for example, a temperature of the skin in the region to which the EIM probe is applied, the moisture content of the skin in this region and pressure with which the EIM probe is applied. Furthermore, measurements of electrode contact quality reflecting how closely the electrodes of the electrode array of the EIM probe contact the skin of the region being analyzed may be obtained. However, it should be appreciated that any other suitable parameters may be obtained in addition to impedance measurements obtained using the EIM probe.

In some embodiments, the EIM measurement system may comprise one or more suitable sensors to measure a temperature of the skin to which the EIM probe is applied. Variations in the skin and tissue (i.e. muscle) temperature may affect impedance measurements. Accordingly, temperature of the limbs or other parts of the patient's body can be adjusted to a specific temperature (e.g., 34° C.), which may be inconvenient and cumbersome. Accordingly, including a temperature sensor, such as a thermocouple or other suitable device, within the EIM probe may allow performing measurement of the skin temperature simultaneously with the impedance measurements. One or more of suitable temperature sensors may be placed in any suitable location in proximity to the electrode array of the EIM probe. Thus, in some embodiments, the temperature sensor may be placed in the center of the electrode array. Though, it should be appreciated that embodiments of the invention are not limited in this respect and temperature sensor may be placed in any suitable location within or near the electrode array.

In embodiments of the invention where measurements of a temperature of the skin are obtained along with impedance measurements, the impedance measurements may be adjusted in accordance with variations in the temperature of the skin that may occur during taking EIM measurements. In some scenarios, an automatic adjustment (or correction) for the variations in the temperature may be performed so that EIM measurements are presented to a user as adjusted, or corrected, values for the variations in the temperature of the skin of the patient. Such adjustment may result in an improved accuracy of the impedance measurements. Also, this may improve an accuracy and reliability of comparison of impedance measurements obtained from a region of a patient's body at different periods of time.

Furthermore, in some embodiments, the ELM measurement system may be used to obtain electrode contact quality measurements indicative of how closely the electrodes of the electrode array of the EIM probe contact the skin of the region where the EIM probe is applied.

It some situations, one or more electrodes of the electrode array may not contact the surface of the patient's skin where the EIM probe is applied sufficiently well to obtain impedance measurements with good resolution. For example, the EIM probe may be applied such that the electrodes are positioned at a distance from the surface of the skin that is larger than a predetermined distance at which impedance measurements with good resolution may be obtained. This may occur due to various conditions related to characteristics of the patient's skin. For example, the skin may be dry, callused, injured or abnormal in any other manner that compromises effective electrical transmission and measurement via the electrode array. Other factors may affect quality of the electrode contact as well. For example, when the EIM probe is applied to a surface of a patient's limb, a head of the probe bearing the electrode array may not contact the surface of the skin evenly so that one or more of the electrodes of the electrode array may not be in contact with the surface of the limb curve. In some circumstances, reliable impedance measurements may not be obtained at all.

To account for the above conditions, the EIM measurement system may measure electrode contact quality reflecting how closely each of the electrodes of the electrode array of the EIM probe contacts the skin of the region being analyzed. The electrode contact quality may be measured as a degree of contact between an electrode and a surface of the region being analyzed. The degree of contact may then be compared to a predetermined threshold. Any suitable components and techniques may be used to measure the electrode contact quality. For example, suitable characteristics of the skin in a region to which the ELM probe is applied may be measured. Thus, in some embodiments, the electrode contact quality measurements may include measuring the moisture content of the skin. Any suitable device, such as a hydrometer, may be used to measure the moisture content of the skin.

Other characteristics of the skin may be measured as well. Also, the impedance measurements obtained using the electrodes array may be used to determine the electrode contact quality.

In some embodiments, during impedance measurements using the EIM probe, the EIM system may generate a signal or other indication indicating that a degree of contact of one or more electrodes of the electrode array does not meet requirements of a degree of contact for obtaining EIM measurements of good quality. For example, the one or more electrodes may not contact the skin of the region being analyzed sufficiently closely. Any suitable measure of what constitutes a "sufficiently close" contact may be employed. For example, a threshold degree of contact may be selected to be compared with the measured degree of contact.

The signal may inform a user of the EIM probe performing the impedance measurements of such "faulty" electrodes. As an example, the signal may comprise an audio signal, such as an alarm. Though, a signal of any suitable format may be substituted. Also, other type of example, A suitable correction for the presence of the "faulty" electrodes may then be implemented. In some embodiments, the correction may be implemented automatically, by reconfiguring the electrode array in response to the detection of one or more electrodes of the electrode array that does not contact the skin sufficiently closely, so that the "faulty" electrode of the electrode array is excluded from a group of electrodes used to obtain the impedance measurements. The electrode contact quality measurements may be continuous or via time intervals, and, if it is detected that the "faulty" electrode comes to contact with the skin, this electrodes may be used in the impedance measurements.

Quality and accuracy of impedance measurements obtained using an EIM measurement system may depend on force with which an EIM probe is being applied to a region of tissue. Thus, in some embodiments, the EIM measurement system may, in addition to obtaining impedance measurements, monitor force with which the EIM probe is being applied to a region of tissue. The force may be monitored using any suitable device. For example, one or more pressure sensors may be employed. The pressure sensor may be embedded into or otherwise associated with the EIM measurement system in any suitable manner (e.g., located within the EIM probe) and may be any suitable device.

During the EIM measurements, it may be useful to apply the EIM probe to a region of tissue with uniform force to ensure reproducibility of the results and to facilitate their assessment. The results of the EIM measurements may be easier to compare between different group(s) of muscles of the same patient and/or different patients. Furthermore, the pressure sensor may provide, during a time when the EIM probe is applied to the patient's body, an indication to a user of the EIM probe of a value of the force being applied, including an indication of whether an inadequate, adequate, or excessive force is being applied. Furthermore, more than one pressure sensors may be used to ensure that the pressure is being applied equally to entire surface of the electrode array of the DM probe. The impedance measurements may be adjusted for variations in force with which the EIM is applied to a region of tissue of the patient.

The EIM measurement system may be associated with any other suitable devices that may enhance reliable detection of muscle condition. Thus, electrical impedance tomography techniques may be used in addition to EIM measurements. The electrical impedance tomography may provide insights into further characterization of muscle conditions and may help to discern the structure of the muscle.

For some applications, it may be useful to perform ultrasound measurements in addition to the impedance measurements using the EIM probe. The ultrasound measurements may provide information on variations in orientation and/or thickness of the skin-subcutaneous fat layer. This information may then be utilized to adjust the impedance measurements for these variations. The results of the ultrasound measurements may be combined in a suitable manner with the EIM measurements to provide a more complete analysis of the underlying tissue. In some embodiments, a suitable ultrasound measurement device may be embedded into or otherwise associated with the EIM probe. The ultrasound measurement device may be configured to automatically assess the orientation and/or thickness of the skin-subcutaneous fat layer.

As discussed above, electrodes in an electrode array of the EIM probe may form different patterns, a nonlimiting example of which includes multiple concentric rings. The electrode array may also be of different sizes so that smaller arrays may be used for assessment of conditions of smaller muscles or muscles of children. In the electrode array, the electrodes may be fixedly attached to a base such as a printed circuit board or other suitable base. The base may be rotatable. Though, the electrode array may be designed to be disposable, meaning that the electrode array may be attached to the body of the EIM probe so that the array may be easily removed. Such electrode array may be referred to a disposable electrode array. Thus, the EIM probe may be used with different electrode arrays. Also, the disposable electrode array may be manufactured to be sterile, which may help lower a rink of spreading of infections (e.g., bacterial infections such as those caused by *Staphylococcus aureus*) between patients.

When the EIM probe is adapted to bear a disposable electrode array, the probe may be equipped with a mechanism for easy attachment and removal of the array from the probe (e.g., a head of the probe). In some embodiments, the backing of the electrode array may be made of a firm plastic and the electrodes may be made from different other materials. The electrode array may be then clipped onto the EIM probe via a suitable locking mechanism and then disposed of via a suitable release mechanism when EIM measurements are completed.

FIG. 1 illustrates an example of an apparatus 100 that may be used to perform multi-frequency EIM, according to one embodiment of the invention. Apparatus 100 includes electrodes 112-115, and also circuit 102 that measures and generates electrical signals using signal measurement circuit 104 and signal generation circuit 106. Apparatus 100 may include any components in any arrangement capable of delivering electrical signals and measuring electrical signals resulting from the electrical signals delivered, as the aspects of the invention are not limited in this respect.

In this embodiment, signal generating circuit 106 is coupled to two spaced-apart current-injecting electrodes 112 and 113, which may be applied to region of tissue 108. Using electrodes 112 and 113, an electrical signal is applied to region of tissue 108, for example, by passing an electrical current through the skin and into the region of tissue. The electrical signal that is applied may be any suitable signal, such as a predetermined voltage potential or a predetermined current. The electrodes may be isolated from a supply voltage using a transformer or any suitable device, such that a "floating" signal, and applied to the patient, thus enhancing the safety of the procedure.

In one example, the signal that is applied to current-injecting electrodes 112 and 113 may be a sinusoidally varying voltage having a magnitude of approximately 1 volt (peak-to-peak) and a frequency between 2 kilohertz and 2 megahertz. As a consequence of applying this signal, electric current is injected into region of tissue 108. However, it should be appreciated that these values of voltage, shape and frequency are provided merely by way of illustration, as the invention is not limited in these respects. Furthermore, any suitable circuit and/or technique may be used to generate the electrical signal applied to the region of tissue, as the aspects of the invention are not limited for use with any particular method of electrical signal generation and/or application.

Signal measuring circuit 104 is coupled to two spaced-apart voltage-measuring electrodes 114 and 115. While the generated signal is applied to tissue region 108 by signal generation circuit 106, signal measurement circuit 104 measures a signal at the tissue region using voltage-measuring electrodes 114 and 115. The signal that is measured may be a voltage difference between the two electrodes that results from the generated signal. Any suitable circuit and/or technique may be used to measure the signal, as the aspects of the invention are not limited in this respect.

Circuit 102 may analyze the measured signal and determine a characteristic of the region of tissue based on the measured signal. Any suitable property of the signal may be measured, such as the magnitude, phase, impedance, resistance and reactance or any suitable combination thereof. In some embodiments of the invention, the measured voltage difference at electrodes 114 and 115 may be divided by the current applied through electrodes 112 and 113 to obtain an impedance measurement. Circuit 102 may determine an impedance, resistance, reactance, phase and/or any other suitable property of the region. Based on the measured signal, any of suitable electrical parameters, and/or electrical properties of the region of tissue, circuit 102 may determine a muscle characteristic. For example, circuit 102 may diagnose and/or assess a neuromuscular disease based on any suitable criteria, as discussed in further detail below.

In some circumstances, circuit 102 may display one or more of the determined electrical parameters to facilitate diagnosis and/or assessment by a physician or technician. Circuit 102 may include any suitable components for performing such measurements, calculations, determinations and presentation functions. As one example, circuit 102 may include a lock-in amplifier for impedance measurement, a computer for performing calculations and a display for displaying the results to a human (e.g., a technician or a physician). However, it should be appreciated that any suitable components or combination of components may be used, as the invention is not limited for use with any particular components or configuration of the components.

Figure 2:
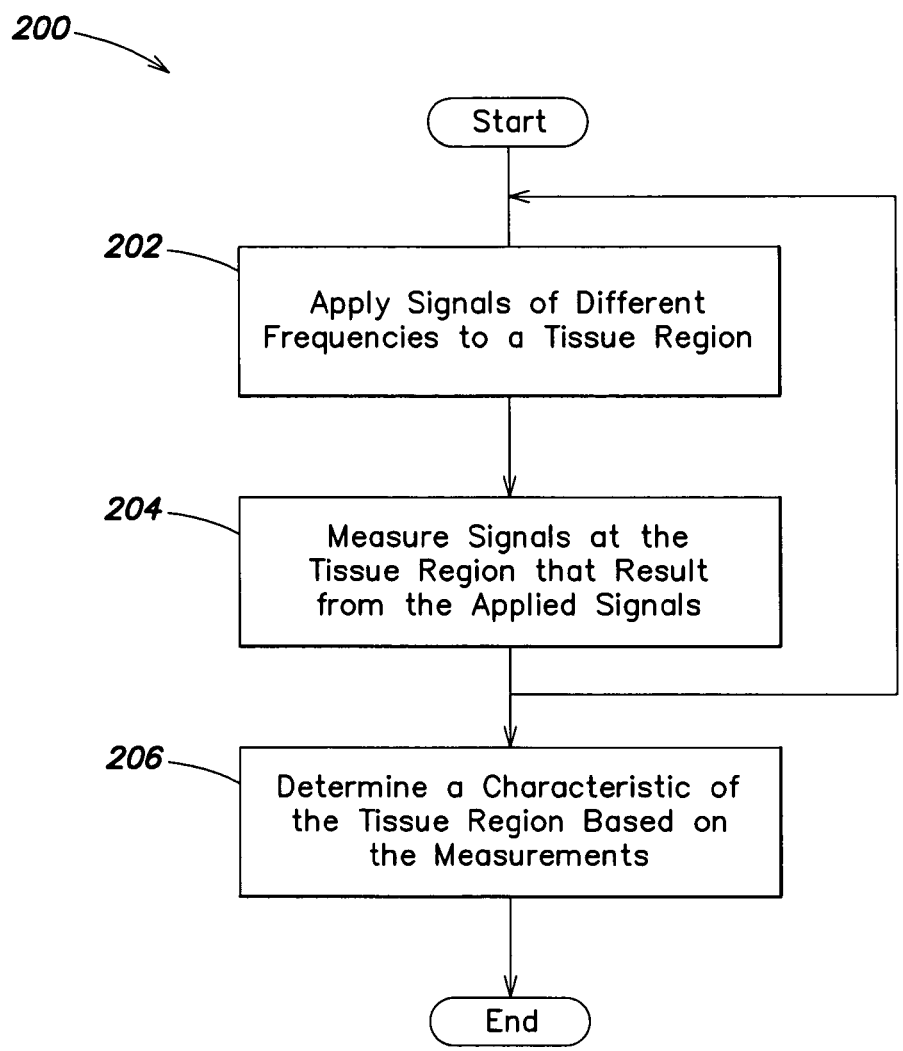
FIG. 2 is a flow chart illustrating a multi-frequency method of determining a characteristic of a tissue region of an organism, according to one embodiment of the invention.

FIG. 2 is a flowchart of a method 200 for performing multi-frequency DM, according to one embodiment of the invention. As described above, a first signal of a first frequency is applied to a tissue region in step 202, and a first signal measurement is made in step 204, such that the measured signal is a result of applying the first signal of the first frequency. Next, a second signal of a second frequency is applied to the tissue region in step 202, and a second signal measurement is made for the second frequency in step 204. Further signals at different frequencies may also be applied, and corresponding measurements may be taken. Any suitable number of frequencies may be used in the multi-frequency EIM procedure, as the invention is not limited as to the number of frequencies measured or the exact frequencies at which measurements are taken. Preferably, if multi-frequency EIM is performed, the frequencies used should be of a number and value such that the measurements are sufficient to provide information useful in assessment or diagnosis of the tissue region, e.g., the assessment or diagnosis of a muscle condition.

In step 206, a characteristic of the region of tissue is determined based on the measurements. The characteristic that is determined may be a muscle characteristic, and may be determined based on one or more electrical properties obtained from the measurements, such as the impedance, phase, resistance and/or reactance of the muscle. As another example, a frequency-averaged impedance, phase, resistance and or reactance may be determined for at least a portion of the range of frequency measurement. The frequency-averaged parameter may be a useful parameter for comparing healthy vs. unhealthy tissue, and evaluating changes in the tissue over time. For example, a diagnosis of a neuromuscular condition may be made based on a frequency-averaged parameter being above or below a threshold value.

One or more electrical properties obtained from measurements taken from the region of tissue as a function of frequency may be used as a signature for the region of tissue. The term signature refers herein to any collection of information obtained from a region of tissue that is characteristic of the tissue. The signature of the tissue, once obtained, may be analyzed to assess, diagnose or otherwise determine a characteristic and/or condition of the region of tissue.

The signature of the tissue may be computationally processed and/or analyzed or presented to a physician or technician for analysis. As one example, a plot of an electrical parameter vs. frequency (e.g., resistance, reactance or phase of the tissue vs. frequency) may be displayed on a computer monitor, and a physician may make a diagnosis based on the plot displayed. Multiple plots displaying any of various electrical properties of the tissue with respect to frequency may be displayed, as the aspects of the invention are not limited in this respect.

Figure 3C:
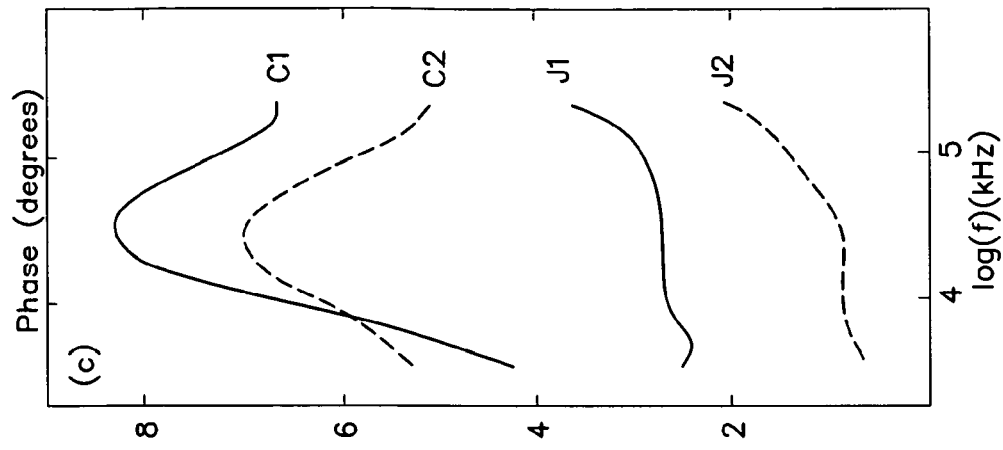
FIGS. 3A-C show plots of measured electrical parameters versus frequency, using multi-frequency electrical impedance myography obtained in accordance with various aspects of the invention.
Figure 3B:
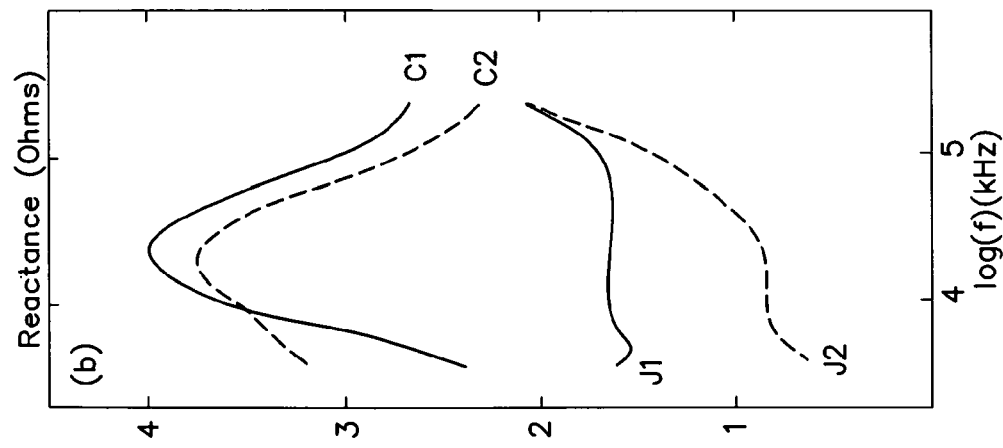
Figure 3A:
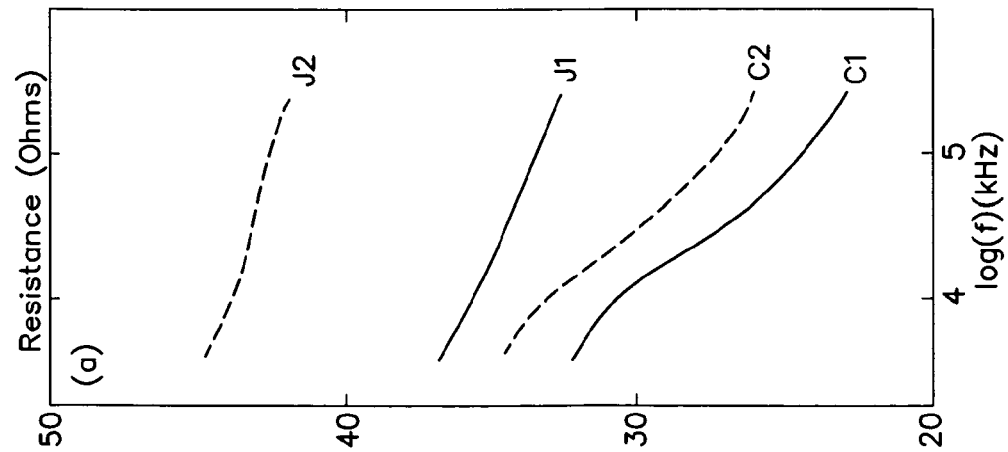

FIGS. 3A-C show plots of resistance, reactance and phase vs. the logarithm of frequency, respectively, measured for two different ALS patients (C and J) at two different visits, 3-4 months apart each. The solid line shows the measurements taken at the first visits and the dashed lines shows the measurements taken at the follow-up visits. Patient C had relatively mild ALS, while patient J had a more severe form of the disease. As can be readily appreciated from FIGS. 3B-C, the patient (J) with the more severe muscle disorder had lower phase and reactance values than the patient (C) with the less severe disorder. At the follow-up visit, both patients exhibited primarily a decrease in both phase and reactance measured, which illustrates the progression of the disease over time.

Additionally, the patient with less severe ALS had a much more pronounced frequency peak in both reactance and phase than the patient with the more severe form of ALS. These results are provided to illustrate various criteria that may be used in determining characteristics of a region of tissue using EIM, and which may displayed for use by a suitable medical practitioner. However, it should be appreciated that any suitable measured and/or calculated criteria may be used for characterization, as the invention is not limited as to the particular criteria used. In some circumstances, a diagnoses or assessment may be made by circuit 102. For example, circuit 102 may be configured to analyze the signature (e.g., one or more electrical properties as a function of frequency) to determine a characteristic of the region of tissue and/or to assess a condition of the region of tissue.

As discussed above, multidirectional (or rotational) EIM may be used for the assessment and characterization of a region of tissue. Multidirectional EIM can be performed by measuring the voltage difference between voltage-measuring electrodes that are arranged with a desired orientation with respect to an axis of the muscle fibers. Both the current-injecting electrodes and the voltage-recording electrodes may have the same orientation with respect to the muscle fibers. The electrical properties of the region of tissue at various orientations may be used to characterize the region of tissue, e.g., to assess a condition of the muscle and/or to perform a diagnosis of the muscle.

Figure 4B:
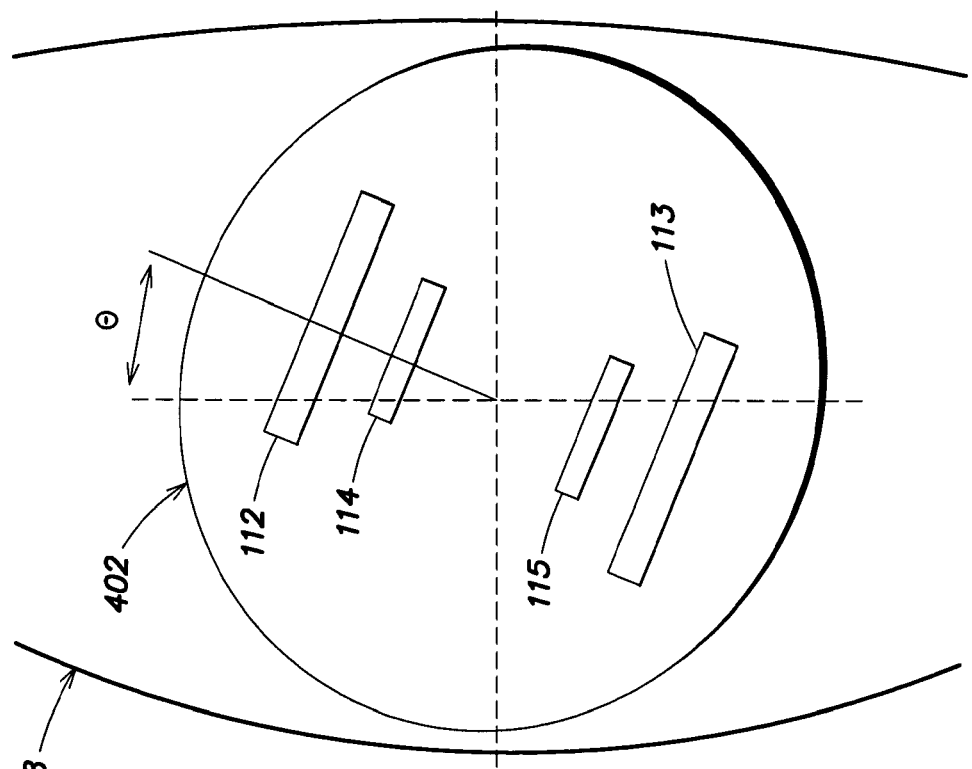
FIGS. 4A-B are diagrams illustrating an example of a device that performs rotational electrical impedance myography, according to one embodiment of the invention.
Figure 4A:
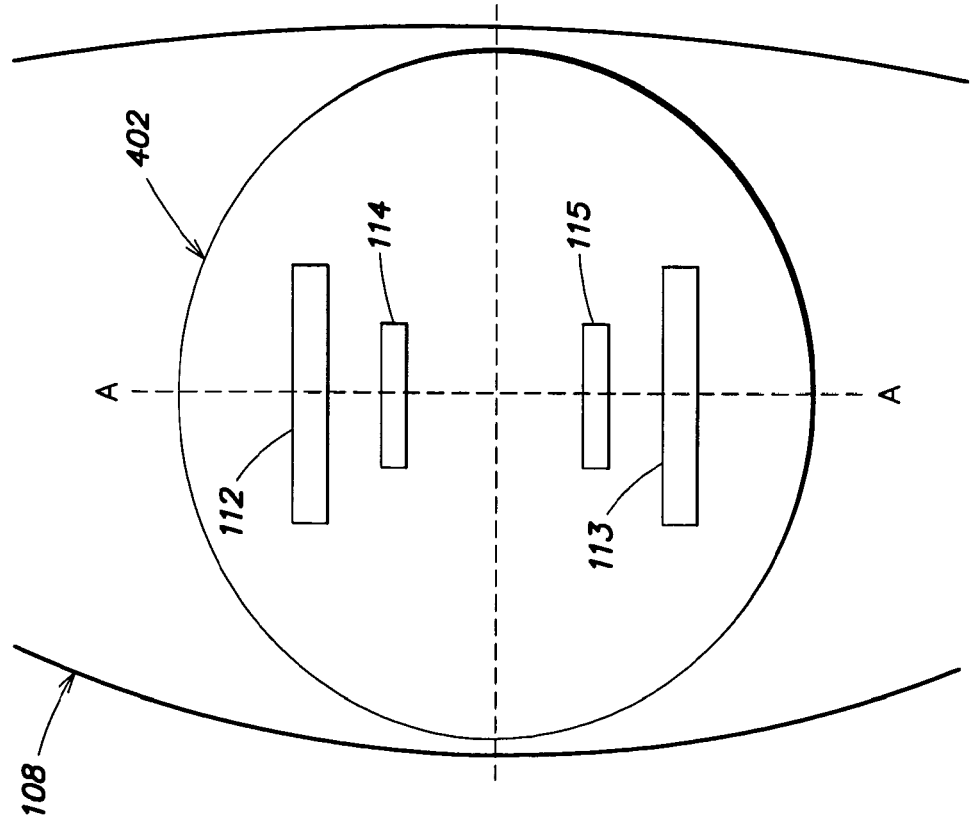

FIGS. 4A-B are diagrams illustrating performing EIM at different orientations with respect to a region of tissue 108. FIGS. 4A-B show electrodes 112-115, as described above with respect to FIG. 1. Electrodes 112-115 may be mounted on a base 402. FIG. 4A illustrates performing EIM along a direction A-A aligned with an axis of the region of tissue 108, e.g., substantially aligned with fibers of the muscle. FIG. 4B illustrates performing EIM along a direction at an angle θ with respect to the axis. Measurements obtained at the different orientations may be used to characterize and/or otherwise assess a condition of the region of tissue 108. Measurements may be obtained at multiple orientations to obtain information about how properties of the tissue vary with orientation (e.g., to determine a degree of anisotropy of the tissue), as discussed in further detail below.

In one embodiment, electrodes 112-115 are mounted on rotatable base 402, which is made of electrically insulating material. When a measurement is to be taken, electrodes 112-115 are brought into contact with the skin at the region of tissue, and are aligned in a first direction with respect to an axis of the region. When a second measurement is to be taken, base 402 is rotated by the desired angle θ, and electrodes 112-115 are again brought into contact with the skin at the new orientation.

Multiple different measurements may be made at different angles. As one example, measurements may be made at six different angles, each 30° apart (0°, 30°, 60°, 90°, 120° and 150°. However, it should be appreciated that any suitable angle increments or number of measurements at different angles may be used, as the invention is not limited in this respect. Preferably, if rotational EIM is performed, the angles used should be of a number and increment such that the measurements are sufficient to provide information useful in assessment or diagnosis of the tissue region, e.g., the assessment or diagnosis of a muscle condition.

In another embodiment, electrodes 112-115 may be mounted on rotatable base 402 made of an electrically conductive material. In this embodiment, the electrically conductive base 402 may be brought into contact with the skin at the region of measurement, and the electrodes themselves may not contact the region directly. In one example, electrically conductive base 402 may be anisotropically conductive such that it preferentially conducts current in a direction perpendicular to the base (e.g., into the patient's body). The anisotropy of the conductive base can prevent undesirable cross-talk between the electrodes, and may allow current to penetrate a greater depth into the tissue region.

Figure 5:
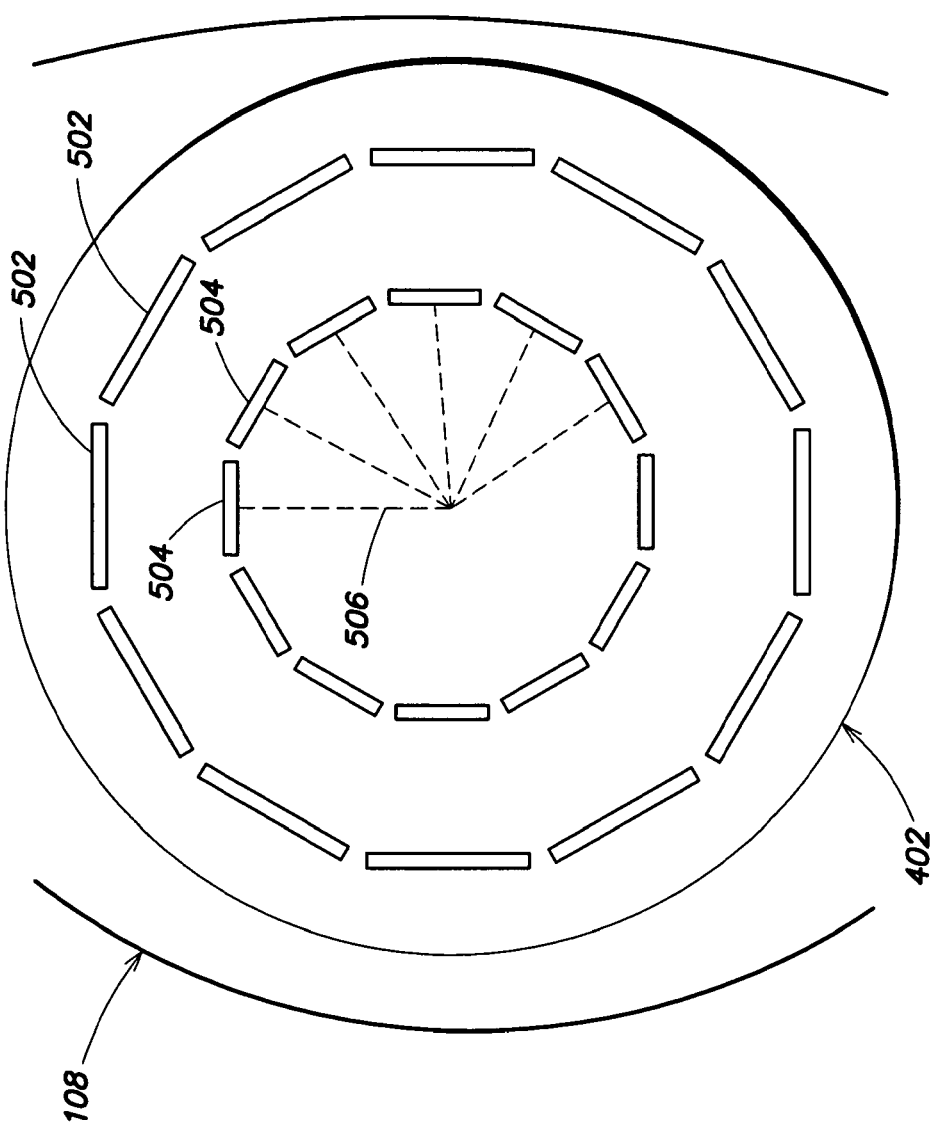
FIG. 5 is a diagram illustrating an example of a device that performs electrical impedance myography at a plurality of angles, according to one embodiment of the invention.

FIG. 5 illustrates another embodiment using rotational EIM, in which a plurality of current-injecting electrodes 502 and voltage-measuring electrodes 504 are mounted on base 402 at different orientations. Since the electrodes are mounted at a plurality of different orientations, it may not be necessary to rotate the electrodes or base 402 to make measurements at different angles. When a first measurement is to be made, an appropriate pair of current-injecting electrodes can be selected and coupled to signal-generating circuit 106 using any suitable switches. That is, the plurality of electrodes may be configured such that the combination of electrodes 502 and 504 at any desired orientation may be selectively activated.

For example, the current-injecting electrodes that lie along line 506 may be selected first. Additionally, the appropriate pair of voltage measuring electrodes 504 that lie along line 506 may be selected, and may be coupled to signal-measuring circuit 104 using any suitable switches. A first measurement may then be taken along direction 506. When a measurement is to be made along a different direction, the switches may be reconfigured to couple different electrodes 502 and 504 to the appropriate circuits, and measurement may be taken at a different orientation.

Figure 6:
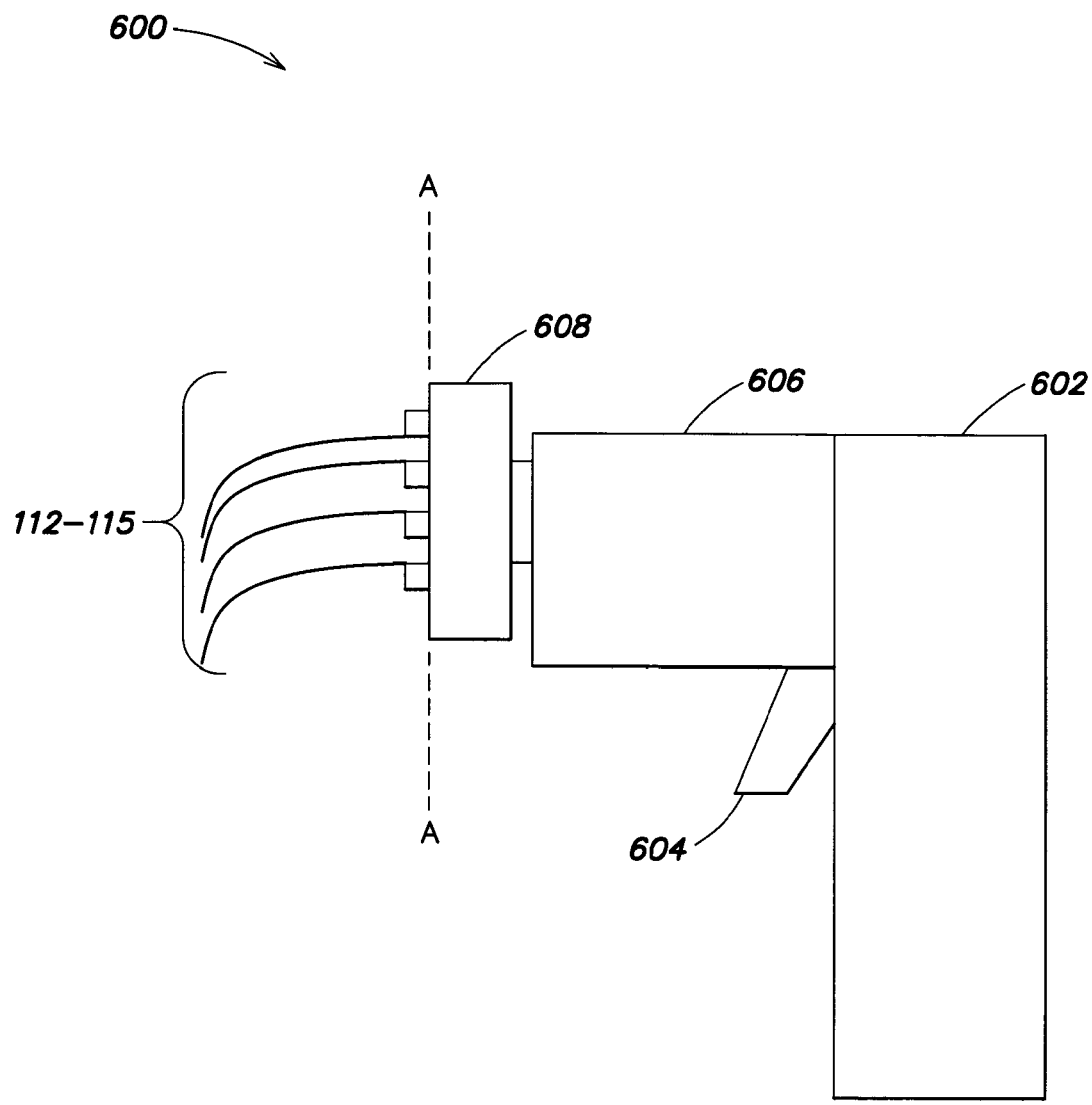
FIG. 6 is a diagram illustrating an example of a hand-held device that performs electrical impedance myography, according to one embodiment of the invention.

FIG. 6 illustrates an example of a hand-held apparatus 600 that may be used for performing EIM, including rotational and/or multi-frequency EIM. Providing a hand-held EIM device may facilitate making EIM measurements, and thus may reduce the amount of time needed to make the measurements. Hand-held apparatus 600 may include a handle 602, a user interface 604, a body 606, base 608 and electrodes 112-115. The electrodes may be coupled to circuit 102 in any suitable way, such as through a cord attached at the bottom of handle 602, for example. FIG. 6 illustrates direction A-A corresponding to direction A-A illustrated in FIG. 4A.

In one embodiment, base 608 may be rotatable, as discussed above, for performing rotational EIM. In another embodiment, base 608 may not be rotatable, but may have a plurality of electrodes 502 and 504 positioned at different orientations, as described in connection with FIG. 5. Apparatus 600 may be configured such that either technique may be used, depending on the type of base/electrode combination that is mounted to the apparatus. In some circumstances, it may be desirable to provide multiple different base/electrode combinations of different sizes that may be easily interchangeable for measuring different types of muscles, or muscles of different sizes. When a different size is needed, the base 608 may be detached from apparatus 600 and another base may be attached.

Figure 7:
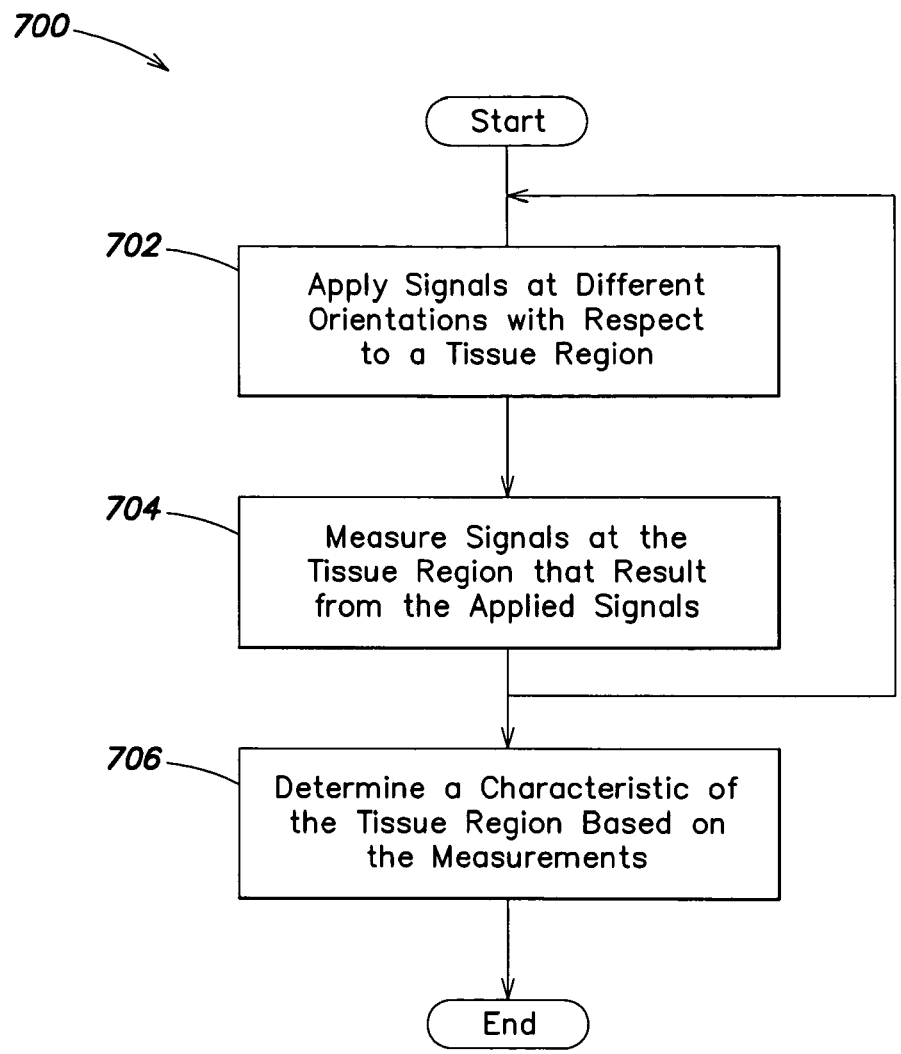
FIG. 7 is a flow chard illustrating a method of performing rotational electrical impedance myography, according to one embodiment of the invention.

FIG. 7 is a flow chart of a method 700 of performing rotational EIM, according to one embodiment of the invention. In step 702, a first signal is applied to a tissue region at a first orientation, and in step 704 a second signal, resulting from the first applied signal, is measured at the region. Next, a third signal is applied to the tissue region at a different orientation. For example, a linear electrode array may be rotated, and another measurement may be made, as illustrated in FIGS. 4A-B. As another example, if a quasi-circular electrode array is used (FIG. 5), a different set of electrodes may be selected that correspond to a different orientation, and a corresponding measurement may be made. It is preferred that at least one measurement be made along a muscle axis, and that at least one measurement be made perpendicular to the muscle axis. Finally, in step 706, a tissue characteristic is determined based on the measurements, using any suitable criteria as discussed above.

The one or more electrical properties obtained as a function of orientation may be used as a signature of the region of tissue. As discussed above, this signature may be analyzed to determine a characteristic of the tissue and/or to assess a condition of the muscle. For example, how the one or more electrical properties vary with orientation (e.g., a degree of anisotropy) may be used to assess the health of the tissue and/or diagnose a condition such as a specific neuromuscular disorder. The signature may be analyzed quantitatively, or compared to a reference signature obtained from known healthy or diseased tissue to assist in the analysis and/or diagnosis of the tissue.

FIGS. 8A-C show plots of resistance, reactance and phase vs. angular orientation, respectively, for both control patients and an ALS patient. As shown in the figures, the measured electrical parameters depend on the orientation of the measurement with respect to an axis of the muscle fibers, with 0° being aligned with the axis. The reactance and phase were lower for the patient with ALS than for the control patients. Additionally, the control measurements exhibited more significant peaks at 90° in both reactance and phase for the control patients than for the patient with ALS. These and/or any other suitable criteria may be used in determining a characteristic of a region of tissue, as these examples are described merely by way of illustration.

In one embodiment, the frequency dependence and orientation dependence of one or more electrical properties of a region of tissue are both exploited to obtain a signature of the region of tissue. For example, at each of a plurality of orientations, an electrical signal may be applied at a plurality of frequencies. Measurements of the tissue may be taken for each frequency at each orientation to determine one or more electrical properties of the tissue at the various frequencies and orientations. By obtaining information about both frequency and orientation dependence, a richer set of indicators may be available to facilitate determining a muscle characteristic and/or assessing a condition of the tissue.

Figure 9:
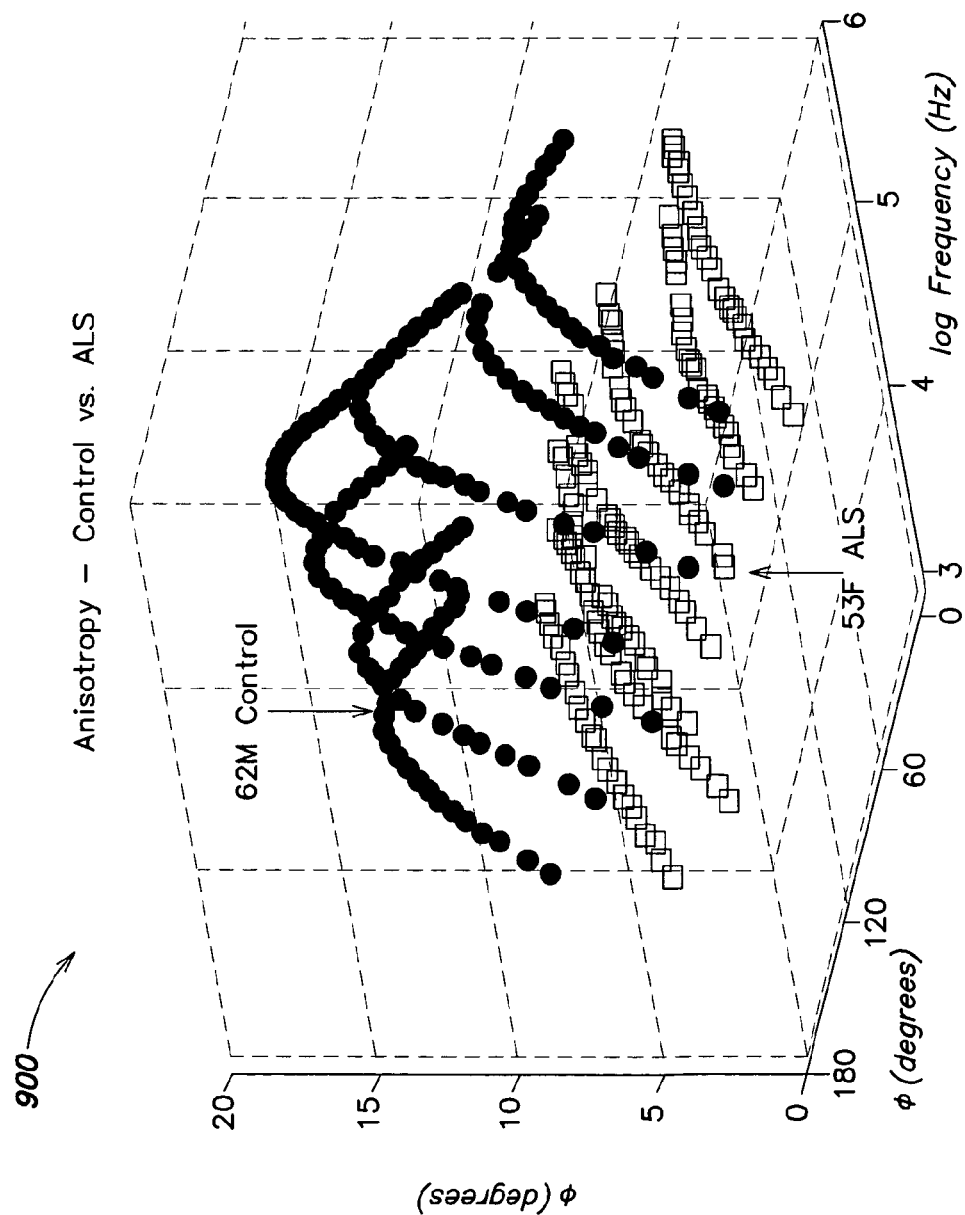
FIG. 9 is a three-dimensional plot of measured electrical parameters versus frequency and angular orientation obtained in accordance with various aspects of the invention.

FIG. 9 shows a three-dimensional plot 900 illustrating the results of performing both multi-frequency and rotational EIM. Overall, the control patient exhibited higher phase measurements and more pronounced phase peaks with respect to both frequency and orientation, as compared to a patient with ALS. Thus, multi-frequency and rotational EIM can be useful, either alone or in combination, for assessing and detecting neuromuscular disorders. In particular, the quantitative nature of the measurements may allow for more accurate assessment and diagnoses of neuromuscular disorders, and also the evaluation of therapies for muscle disorders.

Figure 10:
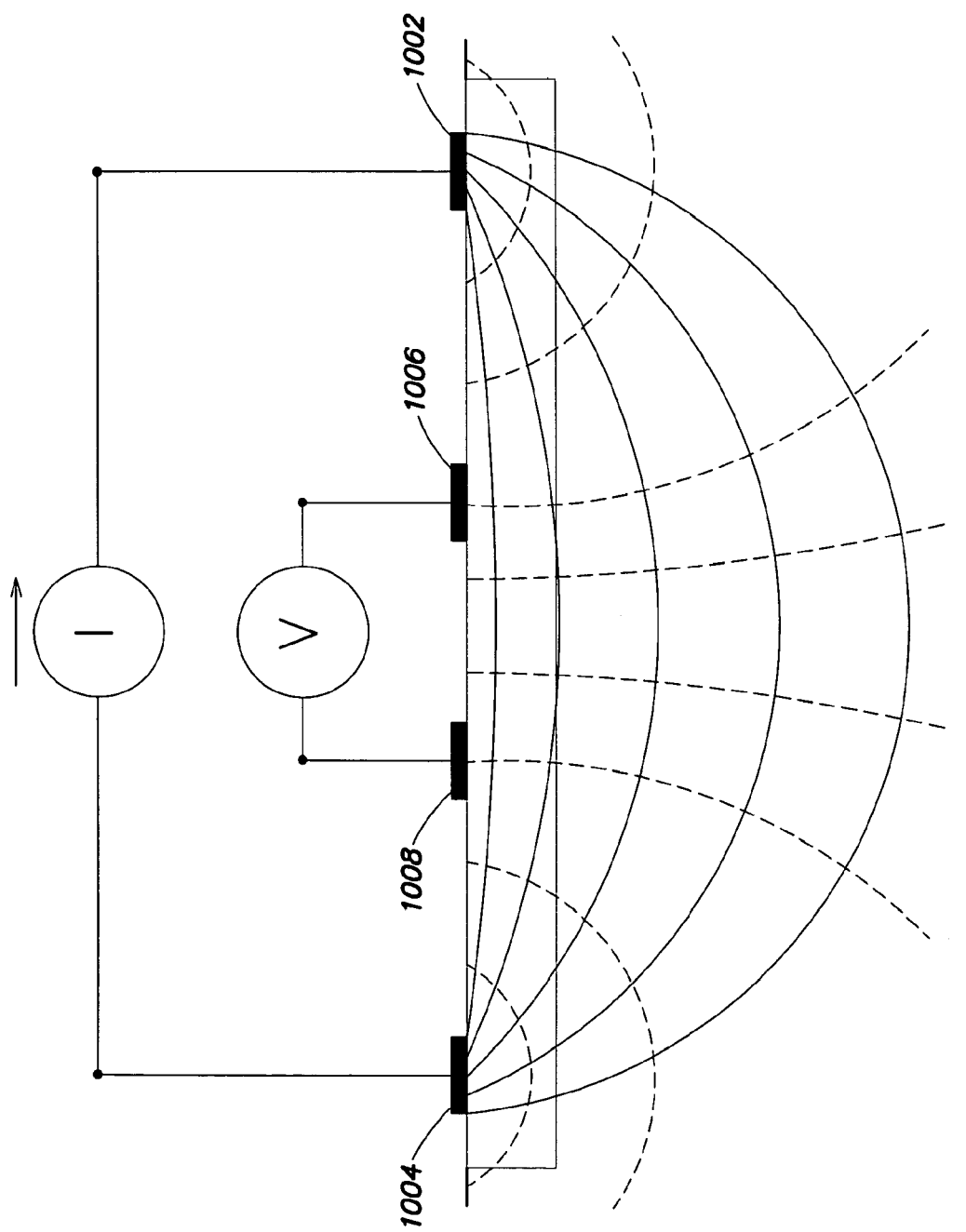
FIG. 10 is a diagram of a tetrapolar measurement setup.

In some embodiments of the invention, a design of the EIM measurement system may be based on a tetrapolar measurement setup known to be used in impedance measurements in biological systems, which is schematically illustrated in FIG. 10. In this exemplary system, impedance measurements may be taken by using a set of, for example, four electrodes arranged parallel to each other. It should however be appreciated that any suitable number of electrodes may be used. In FIG. 10, dashed lines illustrate equipotential lines and solid lines illustrate current flow lines. The shaded region represents a high-resistivity skin-fat layer.

As shown in FIG. 10, two outer electrodes 1002 and 1004 which may be referred to as current-injecting, or excitation electrodes, provide an input signal to a tissue being investigated. This creates an electric potential distribution that may be measured by two inner voltage-recording, or pickup electrodes 1006 and 1008. As compared to a two-electrode measurement, for which the same pair of electrodes provides the excitation current and probes the resultant voltage, the tetrapolar measurement system may allow obtaining improved measurements that are uncorrupted by a contact resistance between the probes and the skin.

Figure 11:
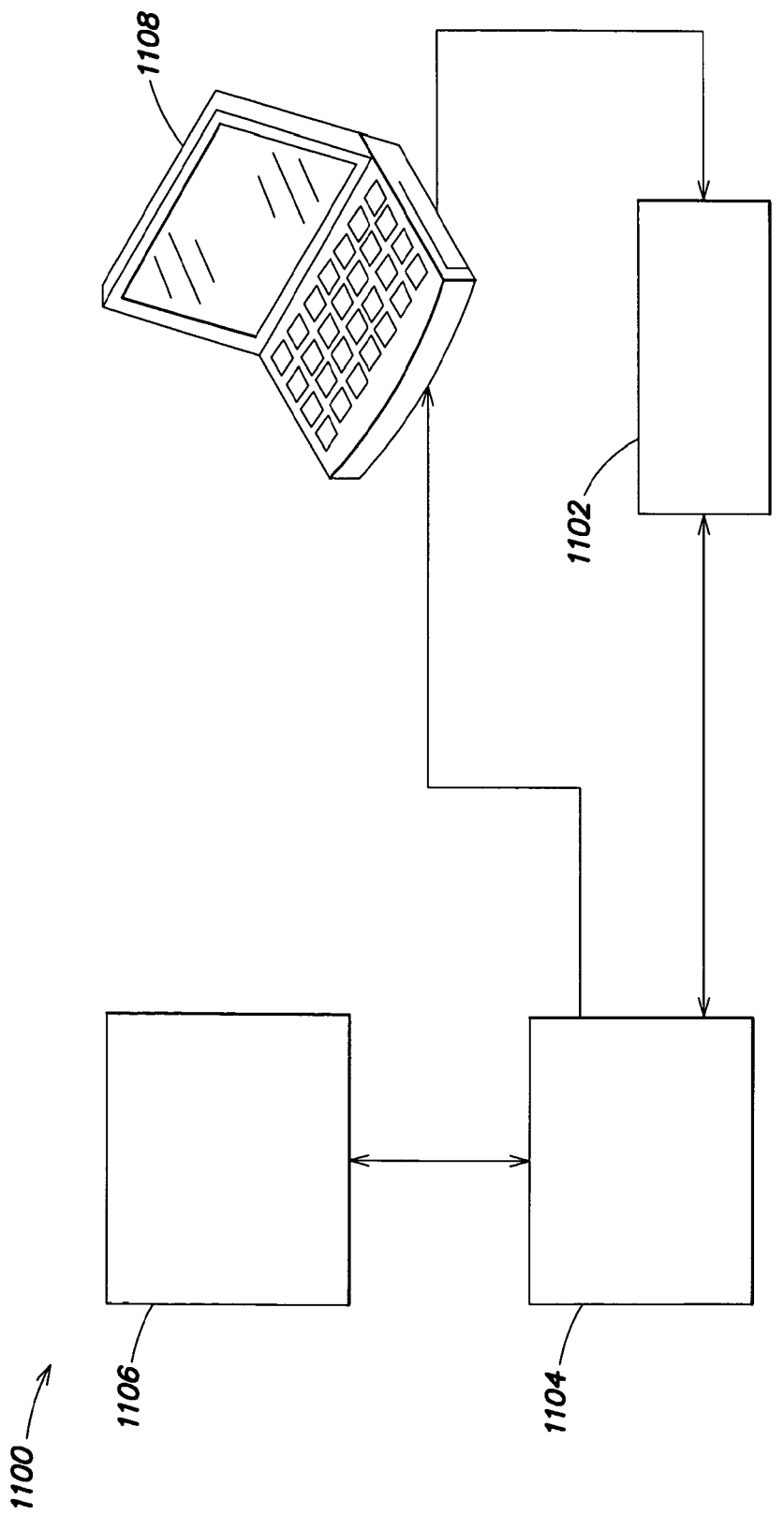
FIG. 11 is a schematic block diagram of an EIM measurement system, according to some embodiments of the invention.

In some embodiments, the EIM measurement system may comprise, as shown schematically in a system 1100 in FIG. 11, a signal generator 1102, a crosspoint switch network 1104, an electrode array 1106, which may be reconfigurable, and a data acquisition module 1108. Electrode array 1106 may be reconfigurable electronically, manually, or in any other suitable manner. System 1100 may comprise any other suitable components as well, as discussed in more detail below. Electrodes of the electrode array may be located on a head of a portable device. In the array, neighboring electrode elements (e.g., vias, pins, solder pads or other elements) may be connected together (e.g., electrically) to create a so-called "composite electrode." In such an arrangement, multiple electrodes may act a single unit which may be used for signal excitation or pickup. Furthermore, at each configuration of the multiple electrodes, a signal comprising multiple frequencies may be applied to muscle tissue.

In some embodiments, the excitation (e.g., current-injecting) electrodes and pick-up (e.g., voltage-measuring electrodes) of the electrode array may be reconfigurable automatically. Thus, one or more combinations of the electrodes that provide sufficiently high resolution of measurements of the muscle anisotropy may be selected automatically.

In addition, in some embodiments, it may be detected that one or more of electrodes of the electrode array do not contact the surface of the skin of the region being analyzed well enough for these "faulty" electrodes being used in impedance measurements. Accordingly, the electrode array may be reconfigured so that these "faulty" electrodes are not used in the impedance measurements.

Figure 12:
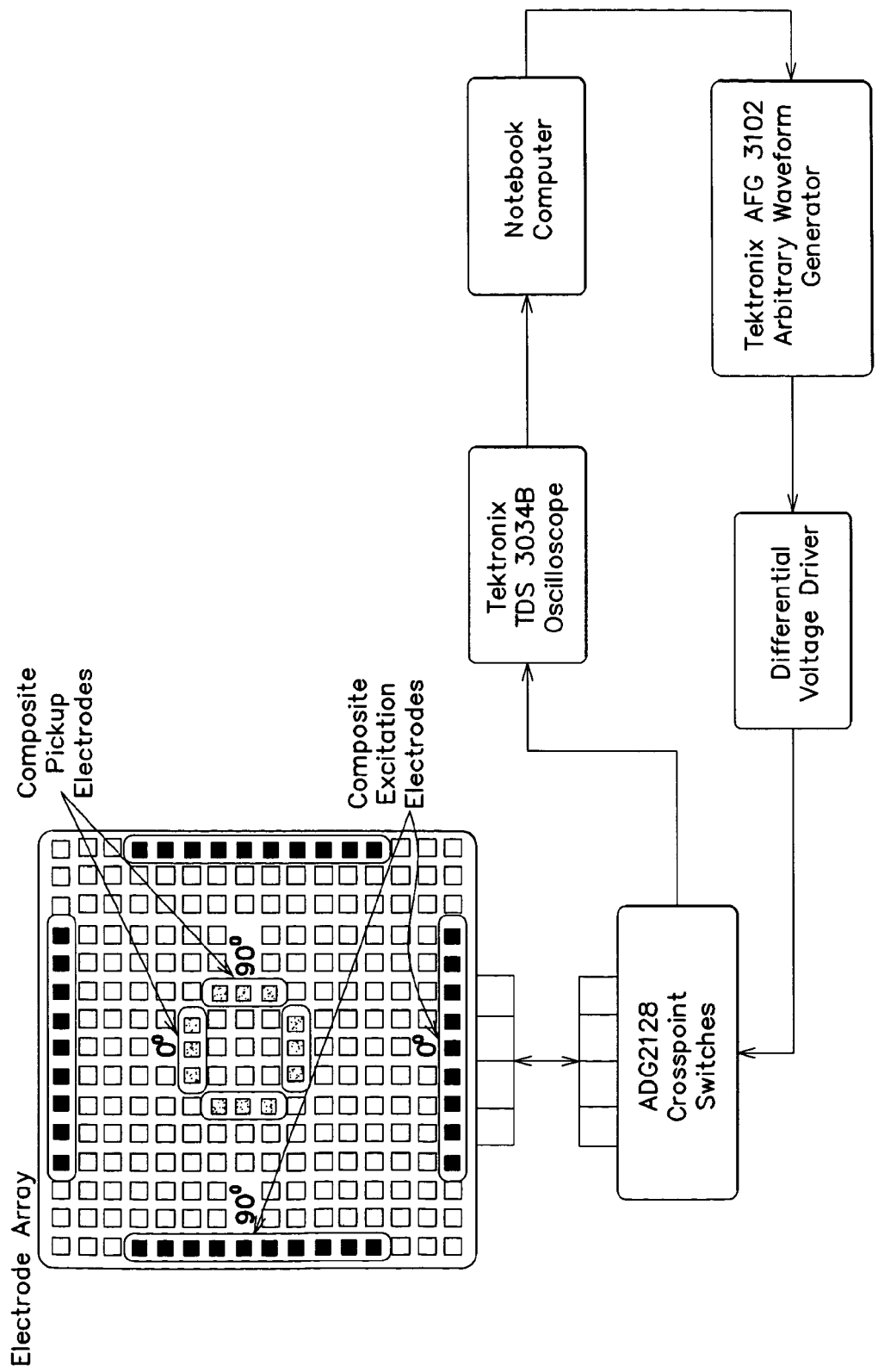
FIG. 12 is a schematic diagram of an EIM measurement system, according to one embodiment of the invention.

An example of a system shown schematically in FIG. 11 is illustrated in FIG. 12, according to one embodiment of the invention. In this example, an excitation signal may be a composite signal comprising multiple tones with logarithmically spaced frequencies. The frequencies may be, for example, from 10 kHz to 4 MHz. Though, it should be appreciated that the frequencies may be lower than 10 kHz or higher than 4 MHz as embodiments of the invention are not limited in this respect. Applying the composite signal may allow obtaining impedance or other measurements easier and faster.

A waveform for this composite signal may be first synthesized (e.g., using MATLAB®, a product of the Mathworks, Inc.) and then downloaded to an arbitrary waveform generator (AWG) such as, for example, Tektronix AFG 3102 AWG. A differential voltage driver may be used to convert the single-ended signal output from the AWG to a differential signal and also to ensure that an amplitude of the differential signal is safe for clinical use. The excitation signal may be applied to a patient's skin via an electrode array. The array may be fabricated, for example, on a printed circuit board. In the system shown in FIG. 12, vias on a printed circuit board may act as electrodes for the EIM measurement system.

As discussed above, the array of the electrodes may be reconfigurable. Thus, both a size and a position of the excitation and pickup electrodes may be reconfigured on-the-fly using a crosspoint switch network or any other suitable component(s). Electrical impedance measurements as a function of angle and frequency may be obtained using the arrangement shown in FIG. 12. A Tektronix TDS 3034B oscilloscope sampling at 10 MS/s may be used as an analog-to-digital converter employed to digitize the measured voltages for further processing on a computer. The computer may be, for example, a notebook computer.

It should be appreciated that any suitable computing device may be used to process measured voltages. However, a use of a mobile computing device allows making the EIM measurement system portable. Mechanically, the EIM measurement system may be designed to fit in the hand of a clinician or any other user so that impedance or other suitable measurements of patient's muscles may be conveniently made at a variety of positions.

In the example illustrated in FIG. 12, the electrode array is shown as a rectangular array by way of example only. It should be appreciated that the electrode array may be of any suitable configuration. Thus, as shown in a photograph on FIG. 13, electrodes located on a head, or an electrode head, of a probe may also be distributed in three concentric rings. Any suitable number of rings, as well as other geometric configurations, may also be used in the electrode array in accordance with various aspects of the invention.

Figure 13:
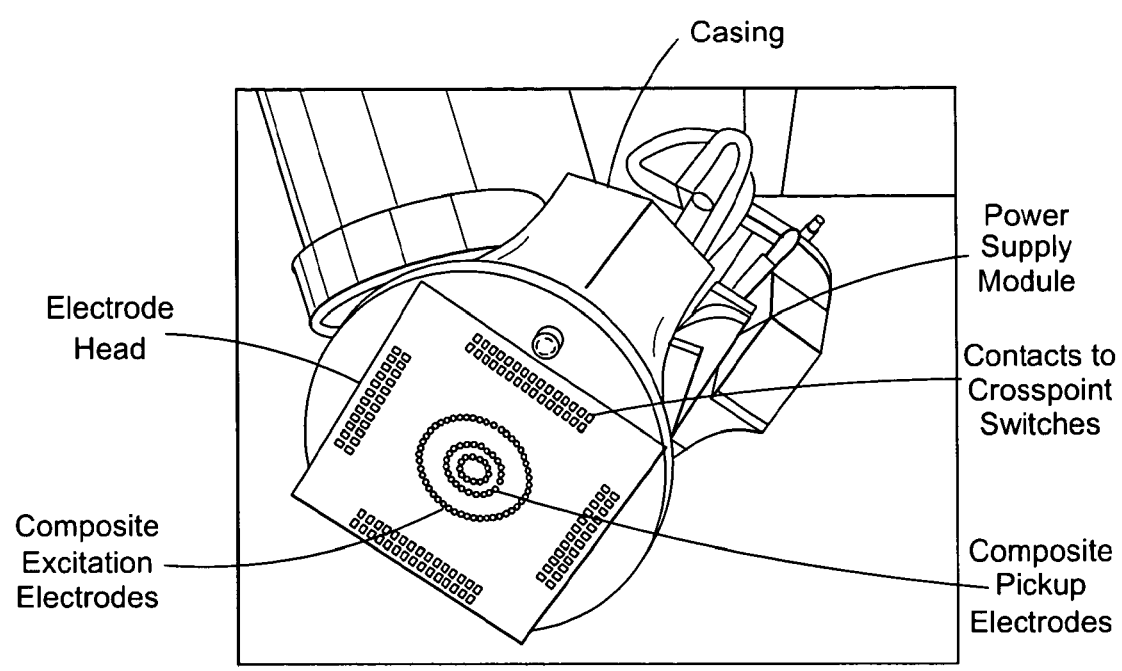
FIG. 13 is a schematic diagram of an EIM measurement system, according to one embodiment of the invention.

In the example of the electrode array shown in FIG. 13, excitation electrodes may be selected from electrode elements that form an outer ring, while pickup electrodes may be selected from electrode elements that form two inner rings. The electrode selection may be accomplished using a crosspoint switch network, as shown in FIGS. 11 and 12. For example, as shown schematically in FIG. 12, several ADG2128 (Analog Devices, Inc., Norwood, Mass.) crosspoint switches may be employed. These components may enable any combination of electrodes to be connected to both the excitation outputs and the detection inputs. Reproducible results may be obtained because the orientation of the composite electrodes with respect to muscle fibers can be altered without physical movement of the electrode head. This makes it possible to accurately alter the direction of current propagation and improve the angular resolution of measurements. The crosspoint switches may be controlled by a computer (e.g., a notebook computer) via, for example, a USB interface. Suitable software may be executed by a processor of the computer to control the crosspoint switches. In some embodiments, the software may be custom designed software.

Figure 14:
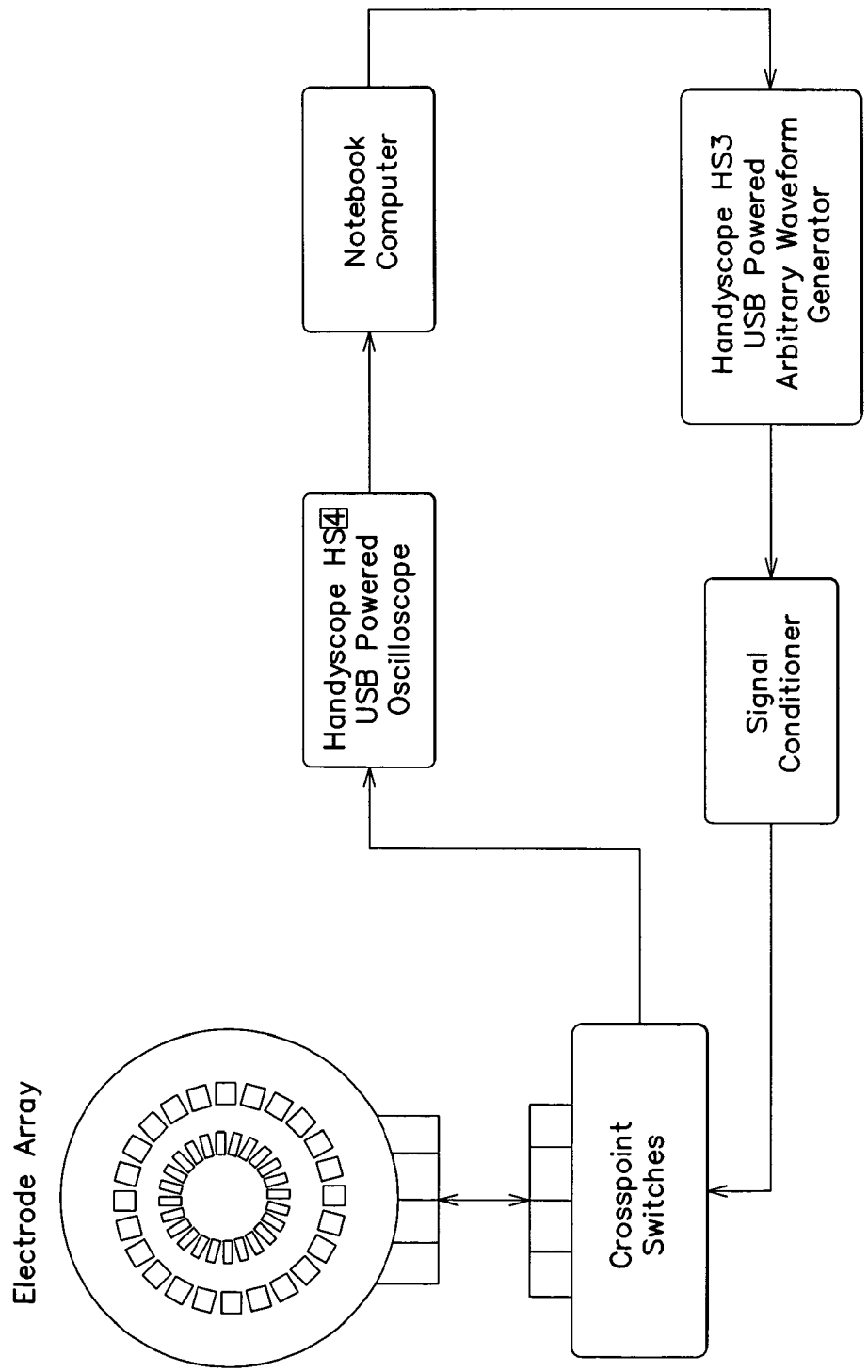
FIG. 14 is a schematic diagram of an EIM measurement system, according to another embodiment of the invention.

FIG. 14 illustrates another example of the ELM measurement system 1100 according to one embodiment of the invention. In this example, measurement and signal generation components comprise portable USB powered components. An excitation signal may be a composite signal comprising multiple tones. For example, the signal may be a composite signal comprising multiple tones with 20 logarithmically spaced frequencies from 10 kHz to 300 kHz. However, it should be appreciated that any suitable number of frequencies of any suitable range may be used. A waveform for this signal may be first synthesized using MATLAB® and then downloaded to a USB powered Handyscope such as Handyscope HS3 (TiePie Engineering, the Netherlands) which has a built-in AWG. A differential voltage driver, shown as "signal conditioner," may convert the single-ended signal output from the Handyscope HS3 AWG to a differential signal and may also ensure that the amplitude of the differential signal (e.g., less than 5 mA) is safe for clinical use.

The excitation signal from the differential voltage driver may be applied to a patient's skin via an electrode array fabricated on a printed circuit board. In this example, each electrode array element may be a solder pad that is electrically connected to one of the input/output pins of crosspoint switches of a crosspoint switch network. The crosspoint switch network may comprise, for example, ADG2128 crosspoint switches. A size and a position of the composite excitation and pickup electrodes may be reconfigured using, for example, $I^2C$ commands sent to the crosspoint switch network by a MSP430 microcontroller (Texas Instruments, Inc., Dallas, Tex.) or by any other suitable controller. The reconfiguration may occur on-the-fly, while the probe is used to obtain measurements from a patient. Electrical impedance measurement as a function of angle and frequency can be accomplished using this arrangement. In this embodiment, a USB powered oscilloscope such as, for example, Handyscope HS4 oscilloscope with four input channels sampling at 50 MS/s may be used as an analog-to-digital converter used to digitize the measured voltages for further processing on a computing device such as, for example, a portable computer. Any other suitable component may be used for this purpose as well.

Figure 15:
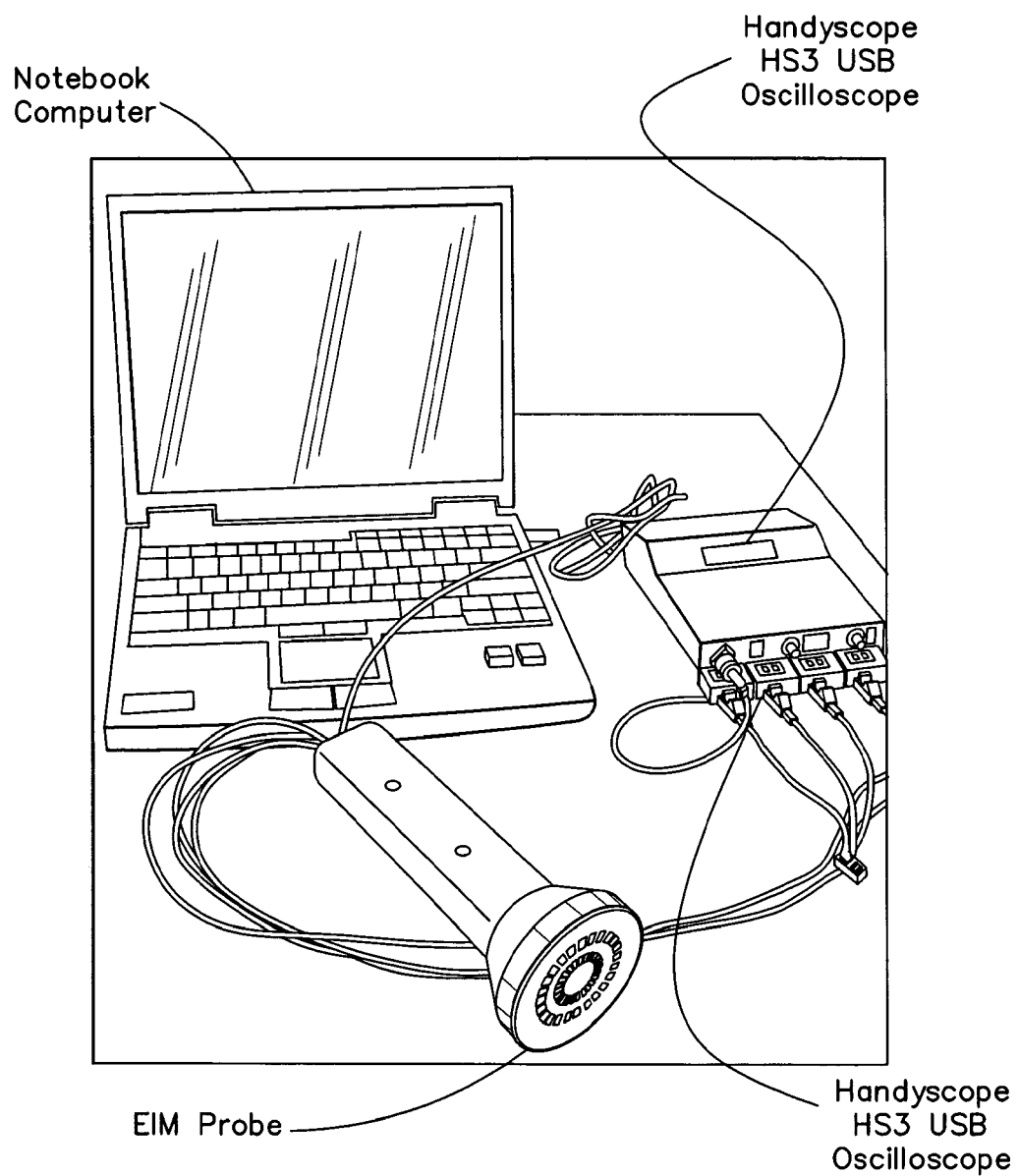
FIG. 15 is a photograph of the EIM measurement system of FIG. 14.

Similarly to the system shown in FIG. 12, the EIM system illustrated in FIG. 14 is portable and may fit in the hand of a user. FIG. 15 is a photograph of the EIM measurement system shown schematically in FIG. 14. All of the components of the system shown in FIG. 15 may be powered by a portable power source such as, for example, a battery, a USB power source or any other suitable power source. Thus, the system may be used as a portable EIM measurements system, with the EIM probe being transferred to a location of a patient or to any other location. This make the system more use-friendly.

Figure 16:
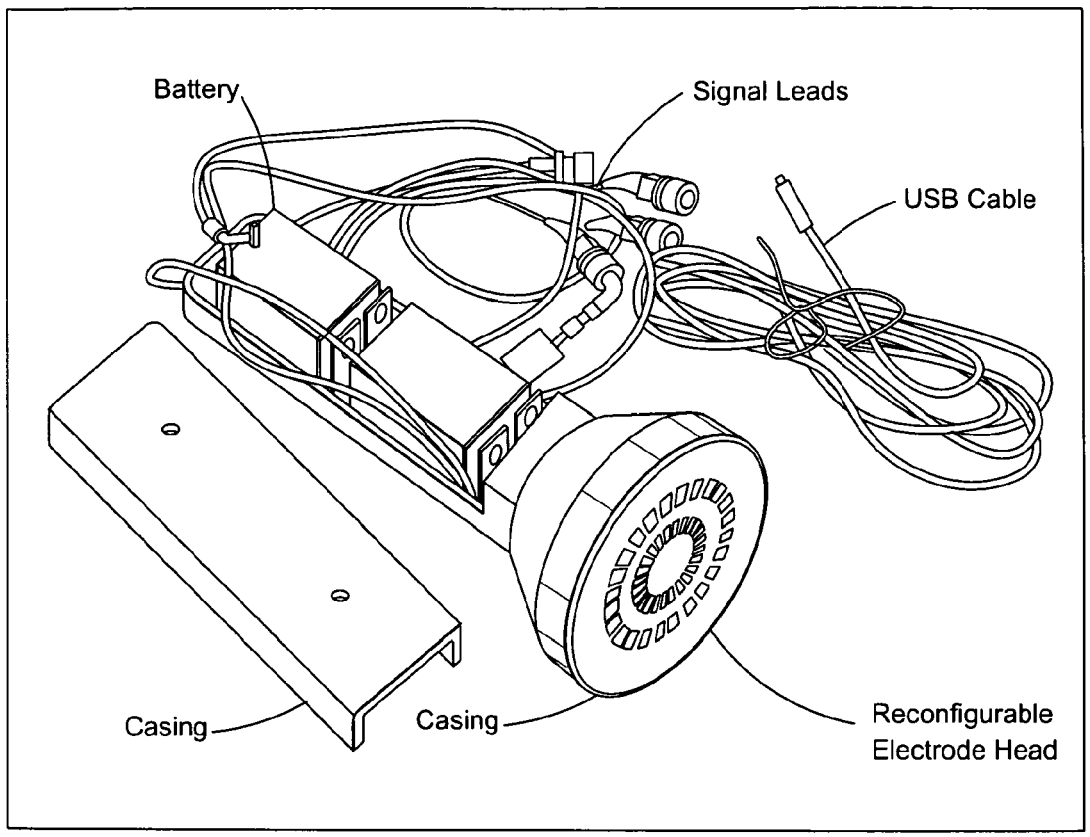
FIG. 16 is a photograph of an example of a probe having a reconfigurable electrode head in accordance with various aspects of the invention.

A photograph of an example of a probe having a reconfigurable electrode head is shown in FIG. 16. This photograph demonstrates that the probe may be powered by a portable power source such as a battery or a USB power source.

Figure 17:
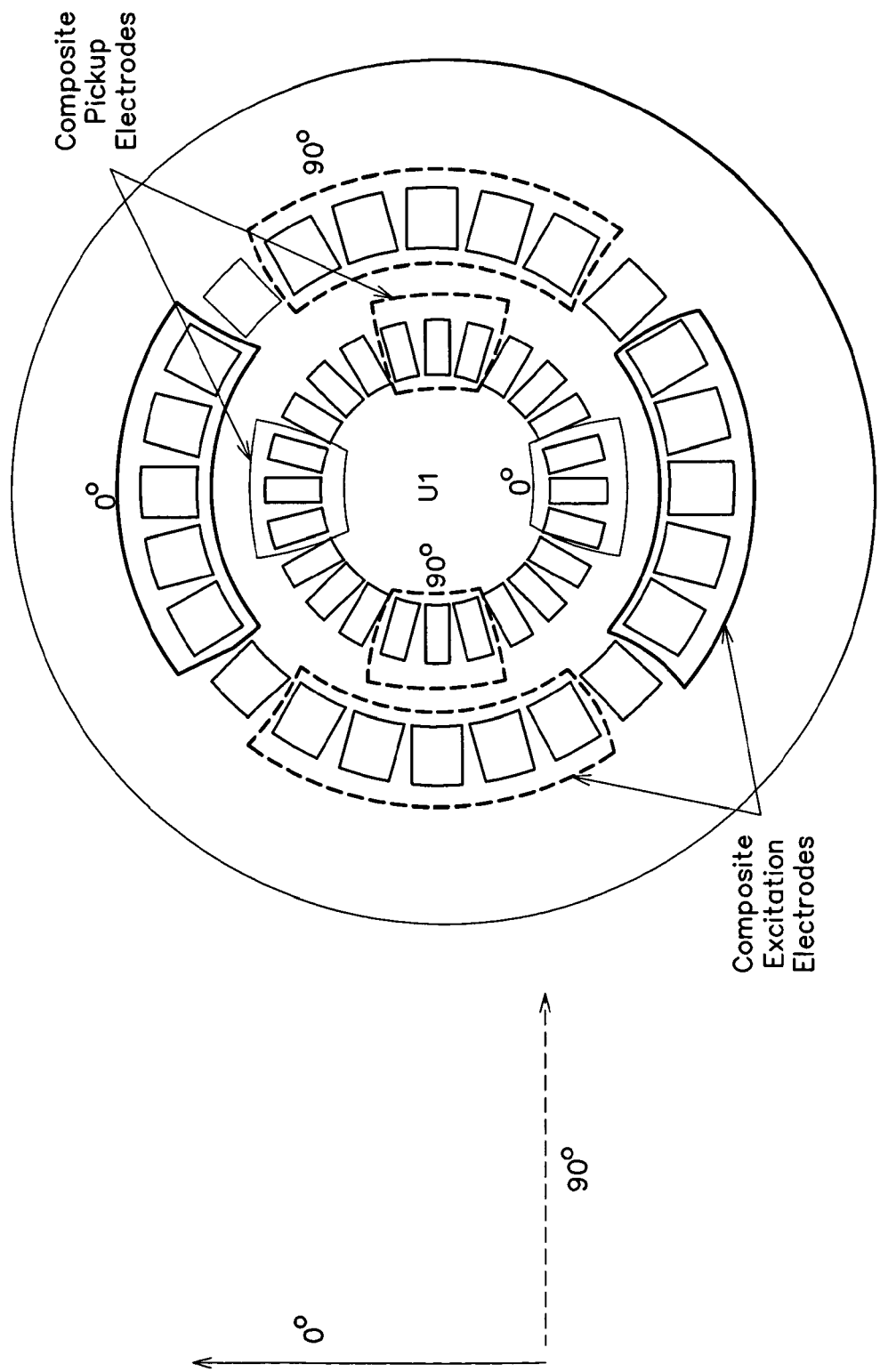
FIG. 17 is a diagram illustrating two examples of composite electrodes elements that may be created, according to one embodiment of the invention.

As discussed above, in some embodiments of the invention, neighboring electrode elements of an electrode array may be connected together to create a so-called composite electrode. The electrode elements of such composite electrode may act as a single unit which can be used for signal excitation or pickup. An example design of an electrode array arranged on a head of the EIM probe illustrated in connection with FIGS. 14 and 15 is shown in FIG. 17.

In this example, two possible patterns of electrode elements that may be created are illustrated. In FIG. 17, four composite electrodes that may be created to make an input signal current to flow along a major muscle fiber direction (for example, 0°) are highlighted with solid lines. To change the direction of the current flow to an angle of 90° with respect the major muscle fiber direction, the old pattern is cleared and a new one is created. This new pattern is shown with dashed lines.

Figure 18:
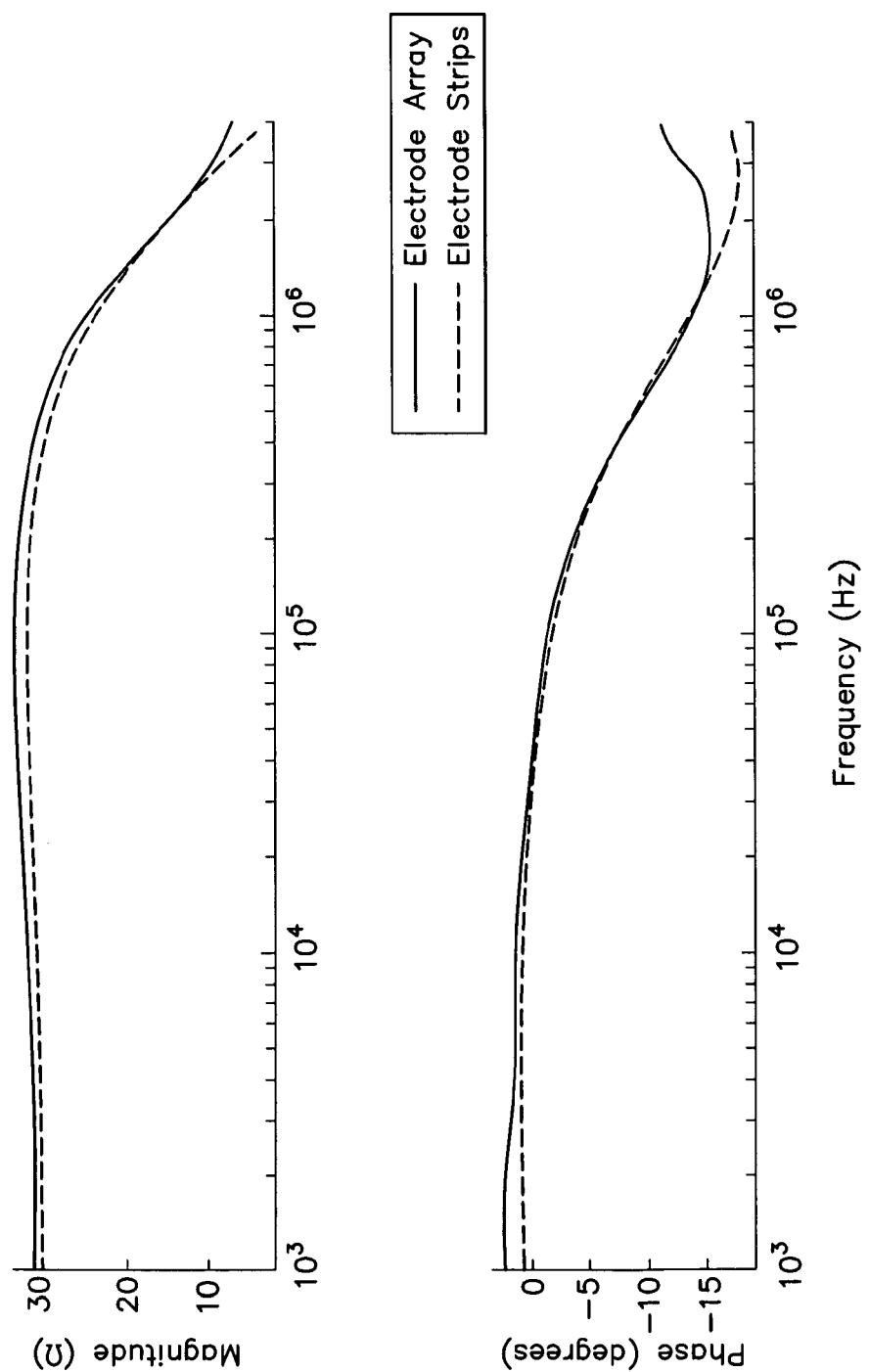
FIG. 18 are impedance plots illustrating EIM measurements taken using solid electrodes and electrically connected multiple electrodes.

Prior experimental results have shown that impedance measurements taken using single solid electrodes were similar to those taken by a series of smaller electrically connected electrodes when they occupy a similar spatial footprint, as shown in FIG. 18. In FIG. 18, both single solid electrodes and electrodes composing an array may be made, for example, from Ag—AgCl. The plots in FIG. 18 demonstrate that impedance measurements taken by the portable EIM system are comparable to those taken by EIM systems in which solid electrodes are used.

Figure 19:
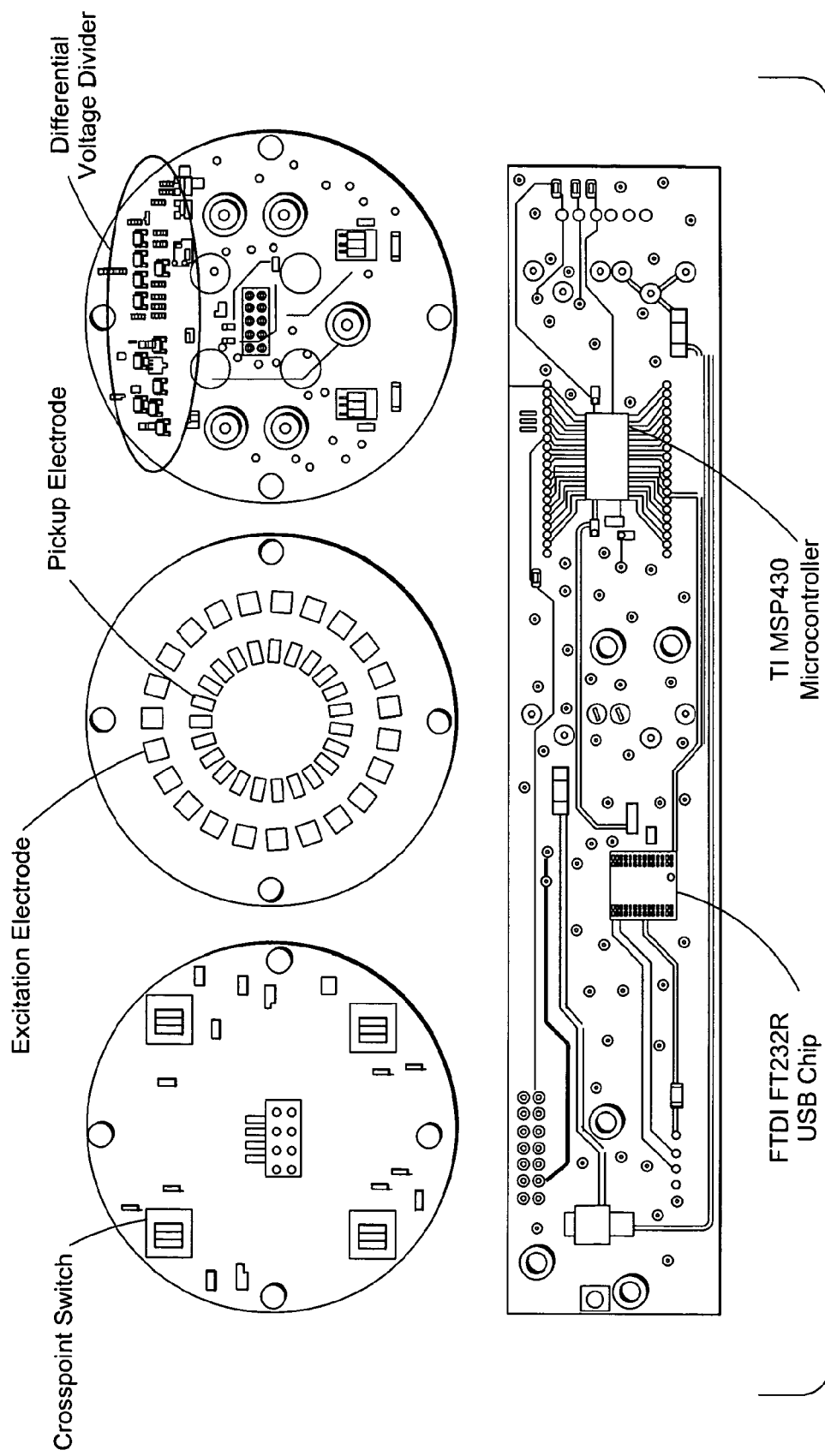
FIG. 19 illustrates components of a reconfigurable electrode head in accordance with one embodiment of the invention.
Figure 20:
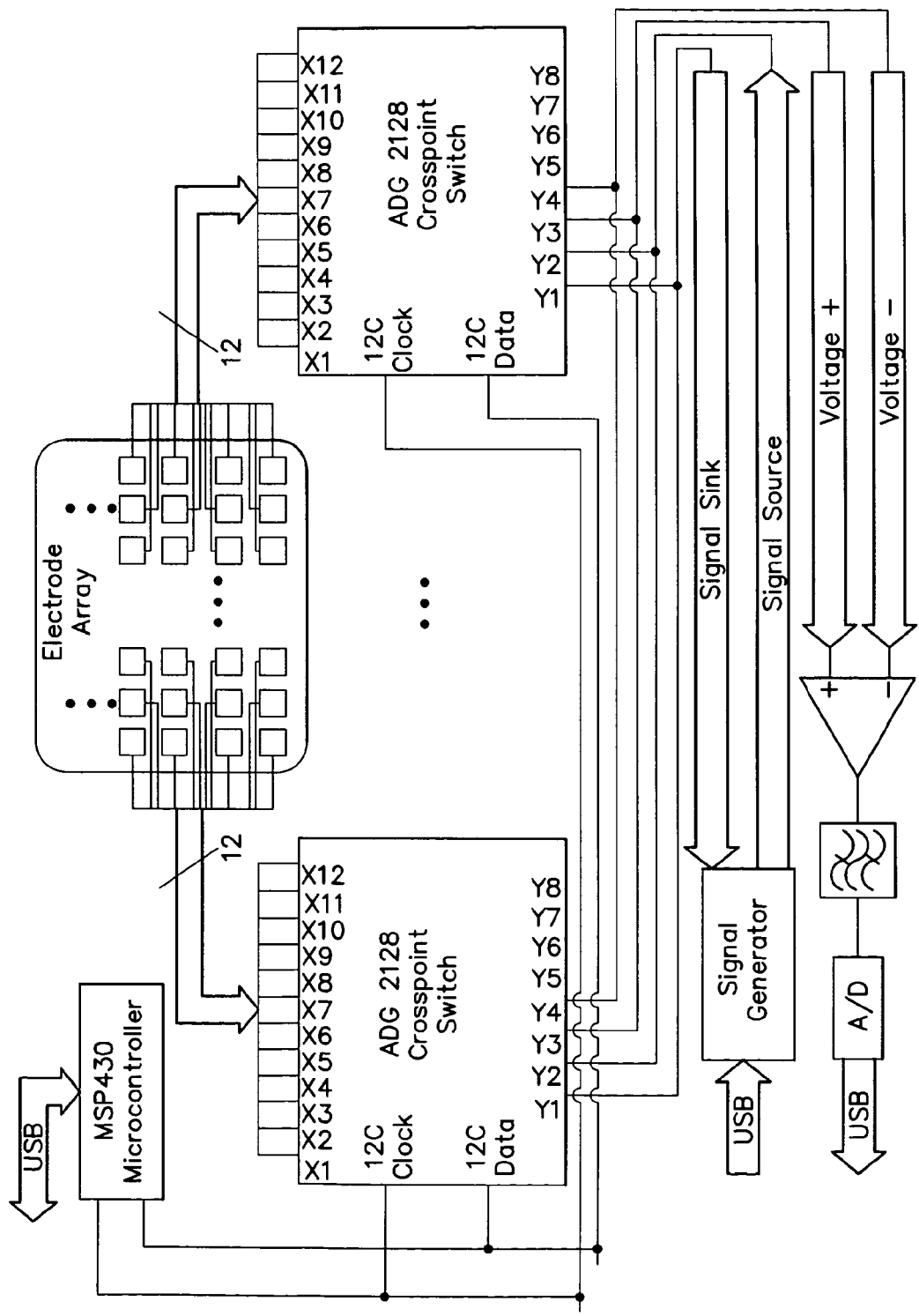
FIG. 20 is a diagram of a reconfigurable electrode head, according to some embodiments of the invention.

In some embodiments of the invention, electrode elements of the EIM system may comprise solder pads on, for example, a printed circuit board. As shown in FIG. 19 illustrating components of a reconfigurable electrode head in accordance with one embodiment of the invention, the electrode elements may be distributed as two concentric rings. In this example, excitation electrodes may be selected from an outer ring and pickup electrodes may be selected from an inner ring. Electrode selection may be performed using, for example, four ADG2128 crosspoint switches (Analog Devices, Norwood, Mass.). Each electrode element may be connected to one of the input/output pins of the ADG2128 crosspoint switches labeled from X1-X12 in FIG. 20.

Systems comprising components shown on FIGS. 14-16 and 19 may enable any combination of electrode elements to be connected to both the excitation outputs (e.g., a differential voltage driver) and the detection inputs (e.g., Handyscope HS4 oscilloscope). Commands required to control operation of the crosspoint switches may be provided by a MSP430 microcontroller (Texas Instruments, Inc., Dallas, Tex.) over an $I^2C$ serial interface. The MSP430 microcontroller may run a firmware (e.g., written in the C programming language) that translates commands from a graphical user interface (GUI) provided by the notebook computer into the $I^2C$ commands for the ADG2128 crosspoint switches. Using these $I^2C$ commands, any pattern of electrode elements may be created. Communication between the notebook computer and the MSP430 microcontroller may be provided via, for example, a FT232R UART USB chip (Future Technology Devices International Ltd., Glasgow, UK). FIG. 18 shows a photograph of an example of chip components used in the reconfigurable electrode head mounted on a custom designed printed circuit board.

An EIM measurement system comprising components shown on FIGS. 14-16 and 19 may allow obtaining reproducible measurement results because orientation of the composite electrodes with respect to the muscle fibers may be altered without physical movement of the electrode head. This may make it possible to accurately alter the direction of current propagation and improve the angular resolution of measurements. For example, an angular resolution of 15° may be achieved.

As discussed above, an EIM measurement system may employ a differential voltage driver that may be used to amplify a signal to a voltage level suitable for application to muscle tissue. Differential signals may be applied to the muscle tissue to reduce common mode interference. This may increase the reliability of the impedance measurements taken with the EIM system.

Figure 21:
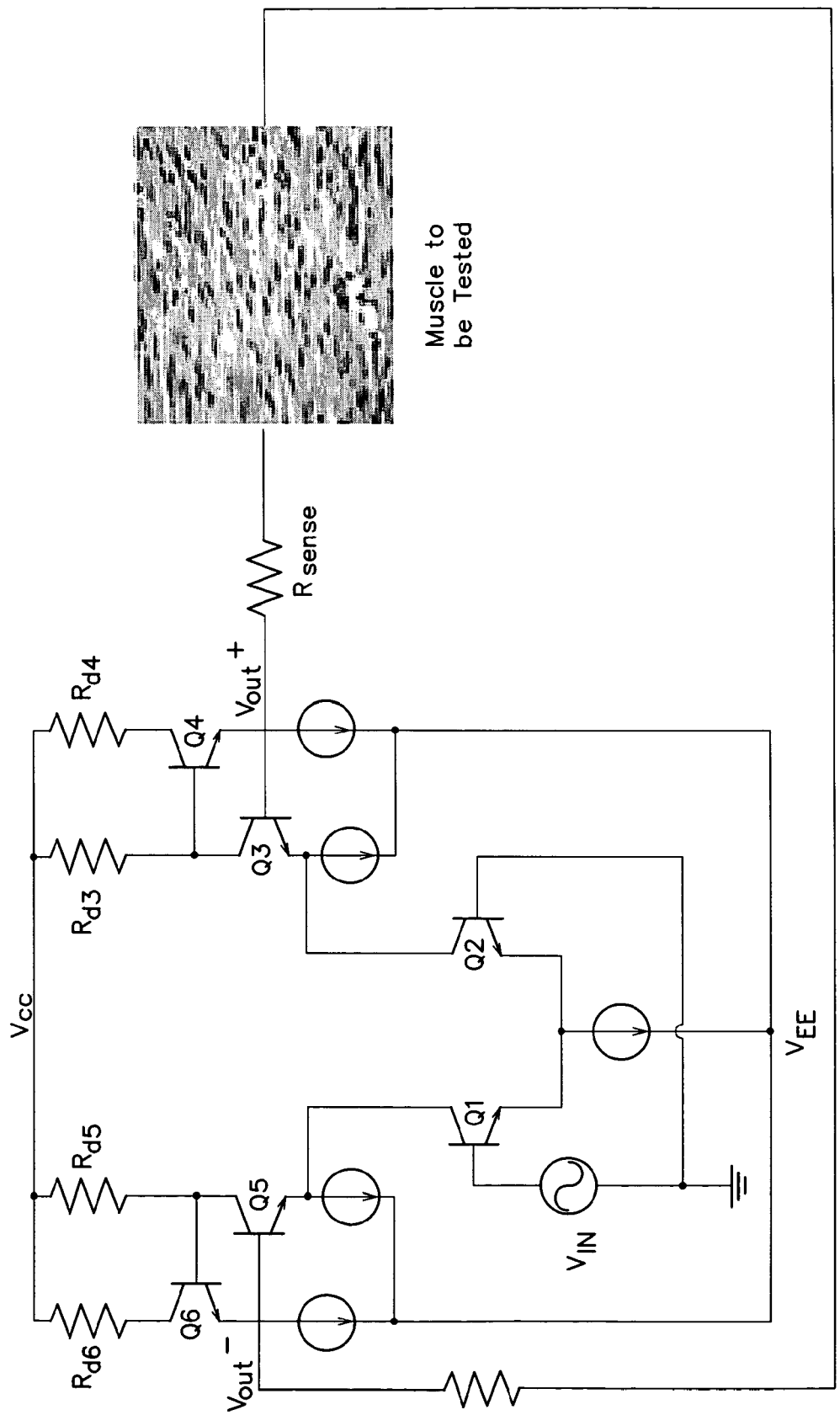
FIG. 21 is a diagram of a differential voltage driver, according to one embodiment of the invention.

In existing current sources, it may be challenging to maintain high output impedance at high frequencies due to stray capacitances. In one embodiment of the invention, a voltage driver, shown in FIG. 21, may perform several functions. Thus, the voltage driver may convert the single-ended signal from the arbitrary waveform generator to a differential signal which may be applied to muscle tissue. The voltage driver may also control amount of current delivered into the muscle tissue to ensure that the amount remains within patient safety limits. In the voltage driver illustrated in FIG. 21, an input stage comprises an emitter coupled transistor pair (Q1, Q2) which converts the single-ended input signal to a differential signal. The signal then passes through the output stage which consists of two transistors in feedback with the base of Q3 connected to the emitter of Q4 and the base of Q4 connected to the collector of Q3. A gain around the feedback loop may be approximately unity but the impedance looking into the emitter of Q4 may be quite small and given by:

$$R_{out} \approx 1/(g_{m3}g_{m4}(r_{o3}\|R_{d3})), \quad (1)$$

where gm3 and gm4 are the transconductances of Q3 and Q4 and ro3 is the output resistance of Q3, respectively. The small impedance at the emitter of Q4 makes this transistor pair a suitable output stage for the voltage driver circuit. It may ensure that very little potential is dropped across the output resistance of the voltage driver so that most of the potential may be dropped across muscle tissue.

Figure 22:
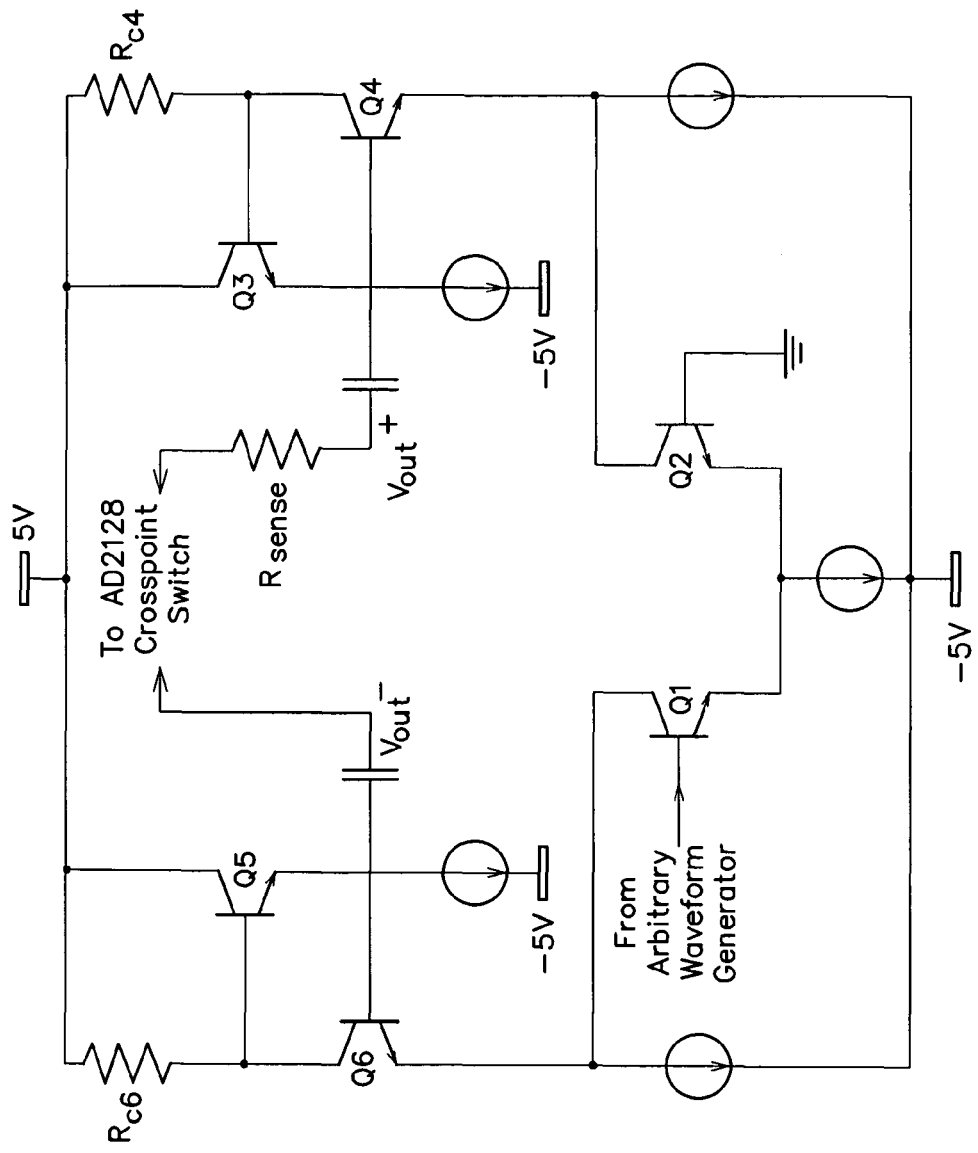
FIG. 22 is a diagram of a differential voltage driver, according to another embodiment of the invention.

FIG. 22 shows a differential voltage driver according to another embodiment of the invention. This voltage driver may be, for example, a low output impedance voltage driver. In this example, an input signal may be applied though a "sense" resistor. A voltage across the sense resistor indicates the current injected. When an ideal current source is used, a system may be more susceptible to stray capacitance at a probe/skin interface. Such stray capacitance may cause a phase shift in the measured voltage that is not due to properties of the tissue, which may compromise integrity of the impedance measurements.

The voltage driver shown in FIG. 22 may perform several functions. Thus, it may convert the single-ended signal from the arbitrary waveform generator to a differential signal which may be applied to muscle tissue. Also, for patient safety, injected current may be limited by current sources at emitters of Q3 and Q5. The input stage consists of an emitter coupled transistor pair (Q1, Q2) which may convert the single-ended input signal to a differential signal. The signal may then pass through the output stage which consists of a cascode device, transistor Q4 and an emitter follower, Q3. The base of Q4 may be connected to the emitter of Q3 and the base of Q3 may be connected to the collector of Q4 (Q5 and Q6 may be identically connected). Using this structure, the base of Q4 may be biased without using another resistor chain. The output impedance of the voltage driver is the impedance looking into the emitter of Q3 (or Q5) which may be quite small and given by:

$$R_{out} = \frac{1}{g_{mQ3}} + \frac{R_{c4}}{\beta_o + 1} \approx \frac{1}{g_{mQ3}}, \quad (2)$$

where $g_{mQ3}$ and $R_{c4}$ are the transconductance and collector resistance of Q3, respectively. The small output impedance, $R_{out}$, of the voltage driver may ensure that most of the excitation signal may be dropped across muscle tissue.

In some embodiments of the invention, a composite signal containing a number of sinusoids with logarithmically spaced frequencies may be used as a signal applied to muscle tissue. Thus, impedance of the muscle tissue under investigation may be measured at multiple frequencies simultaneously. The fact that muscle tissue acts as a linear medium with respect to current excitation makes this approach possible. As a result, a speed of measurement may be increased as compared to an EIM measurement system in which impedance measurements are taken at each frequency sequentially.

As discussed above, one of the parameters that may be used to monitor a progress of neuromuscular disease is a change in a phase of the measured impedance over time. The phase is given by $$\theta = \tan^{-1}(X/R), \quad (3)$$

where X is the reactance and R is the resistance.

This above information may be obtained by taking the Fourier transform of the measured and digitized voltages and performing required numerical computation in the frequency domain. In one embodiment, a MATLAB® script was written to extract the Fourier transform values at the frequencies selected a priori at which impedance information may be measured. The current flowing through the muscle tissue may be obtained by measuring the voltage across the sense resistor, $R_{sense}$ as shown, for example, in FIGS. 21 and 22. The impedance of the muscle tissue may then be computed by taking a ratio of the voltage to the current at each frequency.

Figure 23:
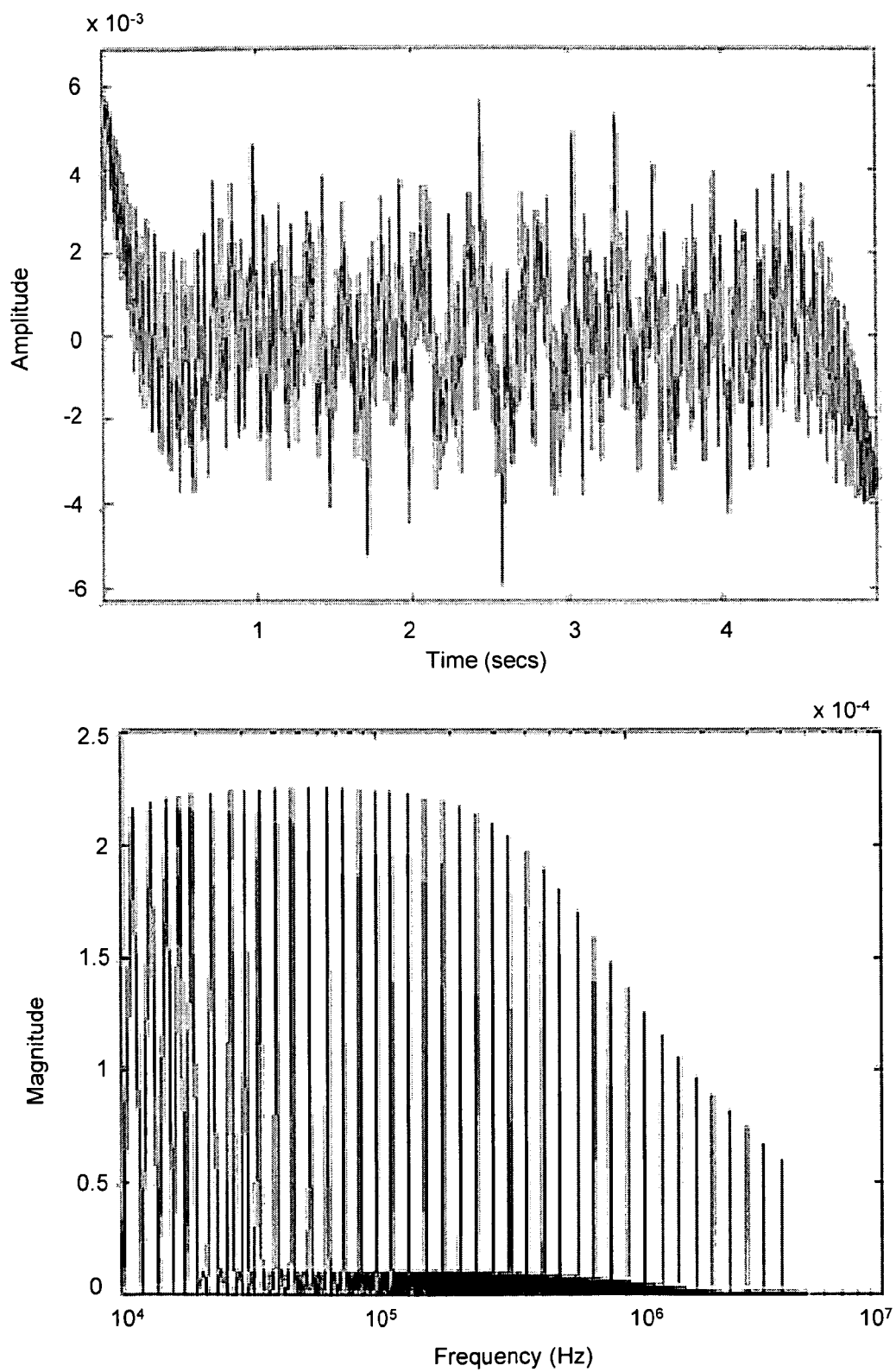
FIG. 23 illustrates time and frequency domain plots of an input composite signal comprising a number of tones at logarithmically spaced frequencies, wherein the input signal is generated using the EIM measurement system of FIGS. 12, 13 and 21.

FIG. 23 shows exemplary time domain and frequency domain (Fourier transform) representation of a composite signal composed of 40 sinusoids with logarithmically spaced frequencies. The signal may be generated, for example, using the ELM measurement system described in connection with FIGS. 12, 13 and 21. An amplitude roll off exemplified in the frequency plot in FIG. 23 shows the low pass transfer function of a voltage driver circuit. Spectral leakage of numerical values into adjacent frequency bins is apparent in the Fourier transform of the measured signals. Typically, in order to prevent the spectral leakage, these tones may need to share an integer factor relationship with the ratio of sampling frequency to number of sample points. In this scenario, this requirement may be relaxed because frequencies at which impedance information is measured are known. A MATLAB® script was written to extract the Fourier transform values at the desired frequencies thus eliminating the effect of spectral leakage. It should be appreciated that this may be performed using any suitable means.

Figure 24:
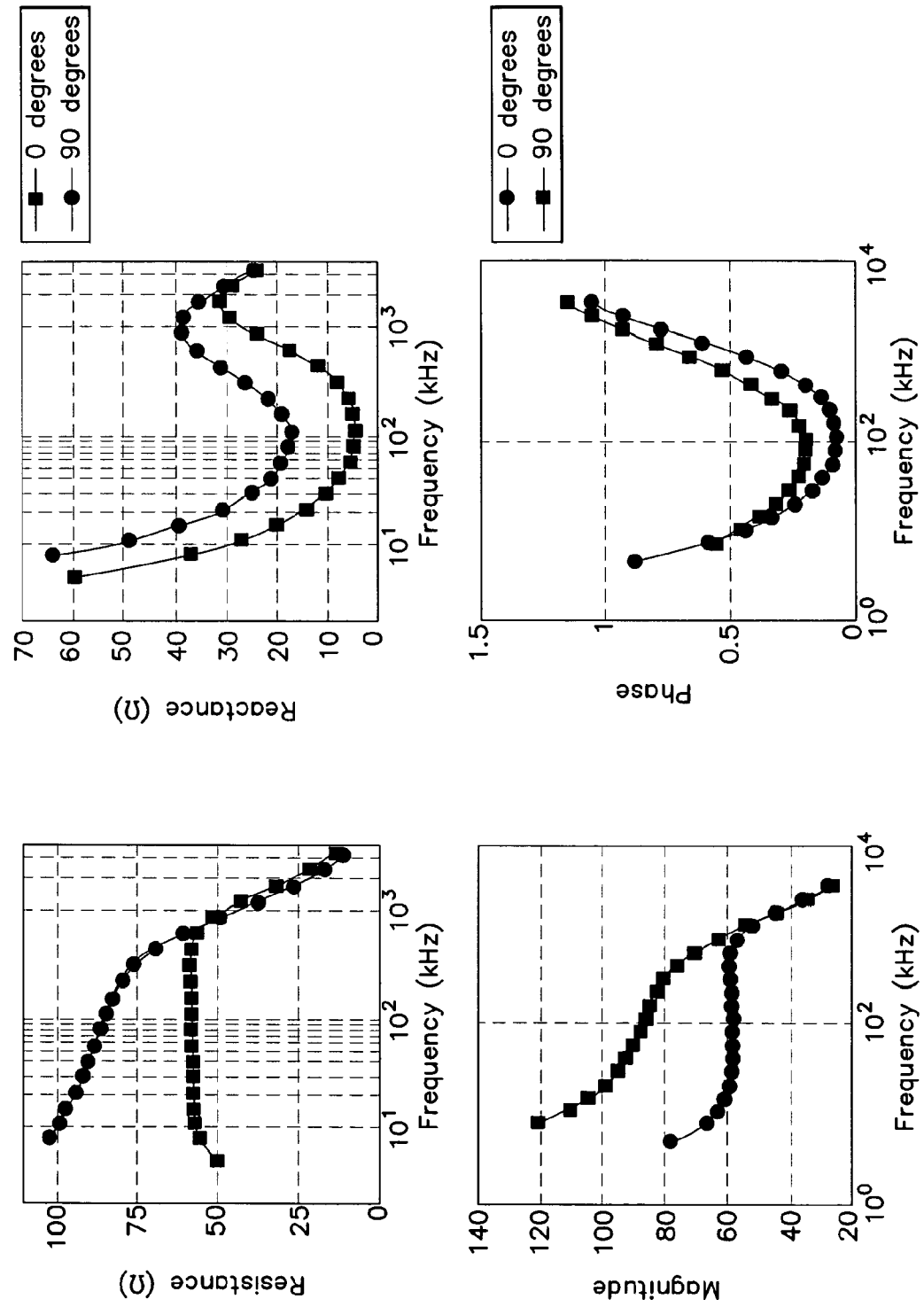
FIG. 24 illustrates impedance plots showing anisotropic current conduction properties of muscle tissue of beef.

Testing of the ELM measurement system, in accordance with some embodiments of the invention, on beef has demonstrated the ability of the system to detect anisotropic conductive properties of muscle tissue at multiple frequencies. Thus, the EIM measurement system described in connection with FIGS. 12, 13 and 21 was used to evaluate impedance of beef (flank steak), results of which are presented in FIG. 24. An expected anisotropy of current propagation in muscle tissue is clearly identifiable. Measurements have been made both aligned to a direction of the muscle fibers (0°) and perpendicular to it (90°). As can be seen in FIG. 24, below the frequency of 1 MHz, both the resistance and reactance at 0° are noticeably lower than at 90°. Intuitively, this result may be expected since current propagation perpendicular to the muscle fibers requires conduction across many muscle cell membranes, each of which adds resistance and capacitance. On the other hand, when current propagates along the muscle fibers it flows mainly through the low-resistance, low-capacitance extracellular space and cell cytoplasm. In the described system, time consuming calibration of the ELM probe for use with different patients or for use with the same patient on different days may not be required. The quantity used in the EIM is the phase of the measured impedance which removes the need to use the actual magnitude of impedance to evaluate the progress of neuromuscular disease. In addition, the contribution of fat and skin to the measured impedance appears as a fixed error added to measurements taken at every angle. Hence, the influence of this error may be mitigated since it affects all measurements equally.

Figure 25:
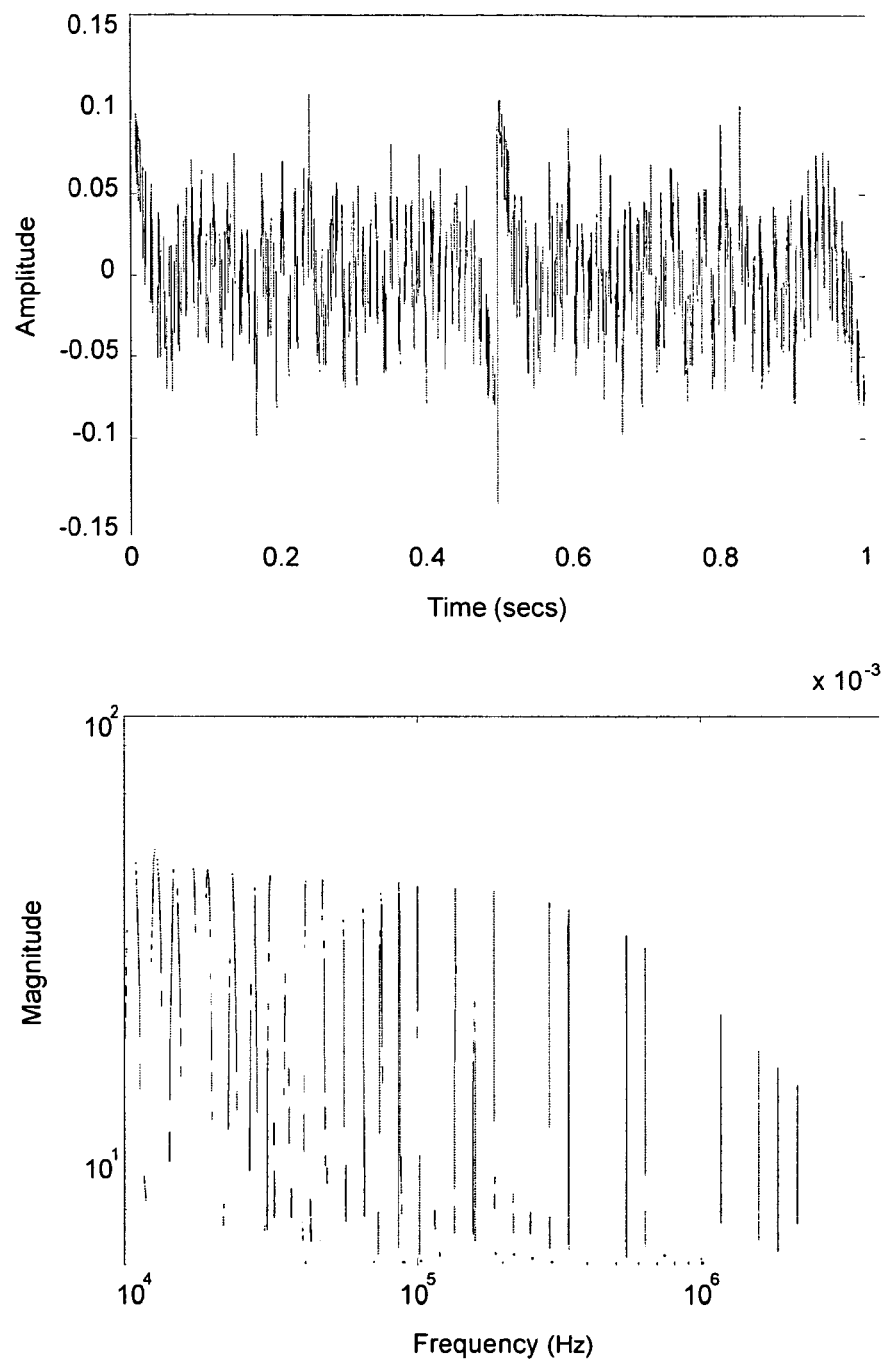
FIG. 25 illustrates time and frequency domain plots of an input composite signal comprising a number of tones at logarithmically spaced frequencies, wherein the input signal is generated using the EIM measurement system of FIGS. 14, 15 and 22.

FIG. 25 shows a time domain and frequency domain (Fourier transform) representation of a measured composite signal composed of 40 sinusoids with logarithmically spaced frequencies. This signal may be generated, for example, using the EIM measurement system described in connection with FIGS. 14, 15 and 22. The amplitude roll off shown in the frequency plot is an artifact of the finite bandwidth of the voltage driver circuit.

As discussed above, results of EIM measurements in accordance with some embodiments of the invention may be displayed to a user (e.g., a physician or other medical practitioner) of the EIM measurement system on a suitable display. The display may comprise any suitable graphical user interface which may be used for visualization and analysis of the results.

In some embodiments, the results may be displayed during operation of the EIM measurement system. Accordingly, the user may view the results of EMI measurements and to thus monitor a progress of analyzing a region of tissue of the patient. Also, the EIM measurement system may monitor the progress of the EIM measurements automatically and may automatically determine when data sufficient to analyze condition of muscle is collected.

Furthermore, once collected, data comprising the results of EIM measurements may be analyzed using different data analysis techniques that allow determining patterns within the data indicative of different muscle conditions.

In order to assess potential clinical value of the EIM measurement system described above, particularly, in connection with FIGS. 14-16 and 22, institutional review board approval was obtained at Beth Israel Deaconess Medical Center and three individuals were enrolled in the study after signing an approved consent form. The results obtained using the above system are shown in FIGS. 26-28, in which data obtained from biceps of a normal subject, a patient with amyotrophic lateral sclerosis (ALS) and a patient with inclusion body myositis are displayed, respectively. The data are taken at logarithmically spaced frequencies between 10 kHz and 300 kHz and at angular increments of 30° from −90° to 90°. Effort was made to orient the 0° axis of the electrode array as close to the main muscle fiber direction as possible.

As can be seen from FIG. 26, the normal subject demonstrates a relative subtle anisotropy in both the resistance and reactance plots (x-axis). A clear frequency dependence is also present, with lower values at higher frequencies for both parameters. As shown in FIGS. 27 and 28, in both of the diseased subjects, this normal frequency dependence is altered, most notably in the reactance, where the values appear to increase at higher frequencies. Thus, it may be noted that reactance curves slope upward and to the right. In addition, in both of the diseased cases, the absolute value of both the measured reactance and resistance are offset from those observed in the healthy subject.

FIGS. 26-28 also illustrate that, in addition to the changes in the frequency dependence, the anisotropic character of the tissue is also different. Since the probe was oriented such that 0° was the major muscle fiber direction in all three individuals, it was anticipated that the lowest resistance and reactance values would occur at that angle. Indeed, in the healthy subject, this general shape of the anisotropy is apparent in both the reactance and resistance traces, as shown in FIG. 26. However, in the ALS patient, a marked distortion and accentuation of the anisotropy of the resistance is observed, with an elevation in the overall values and a minimum at −60° rather than at 0°, as shown in FIG. 27. In the myositis patient, in contrast, the anisotropy actually appears more modest than either the normal subject or the ALS patient, as shown in FIG. 28. Both of these findings illustrate that the anisotropy may be elevated in neurogenic diseases and reduced in myopathic diseases.

Figure 29:
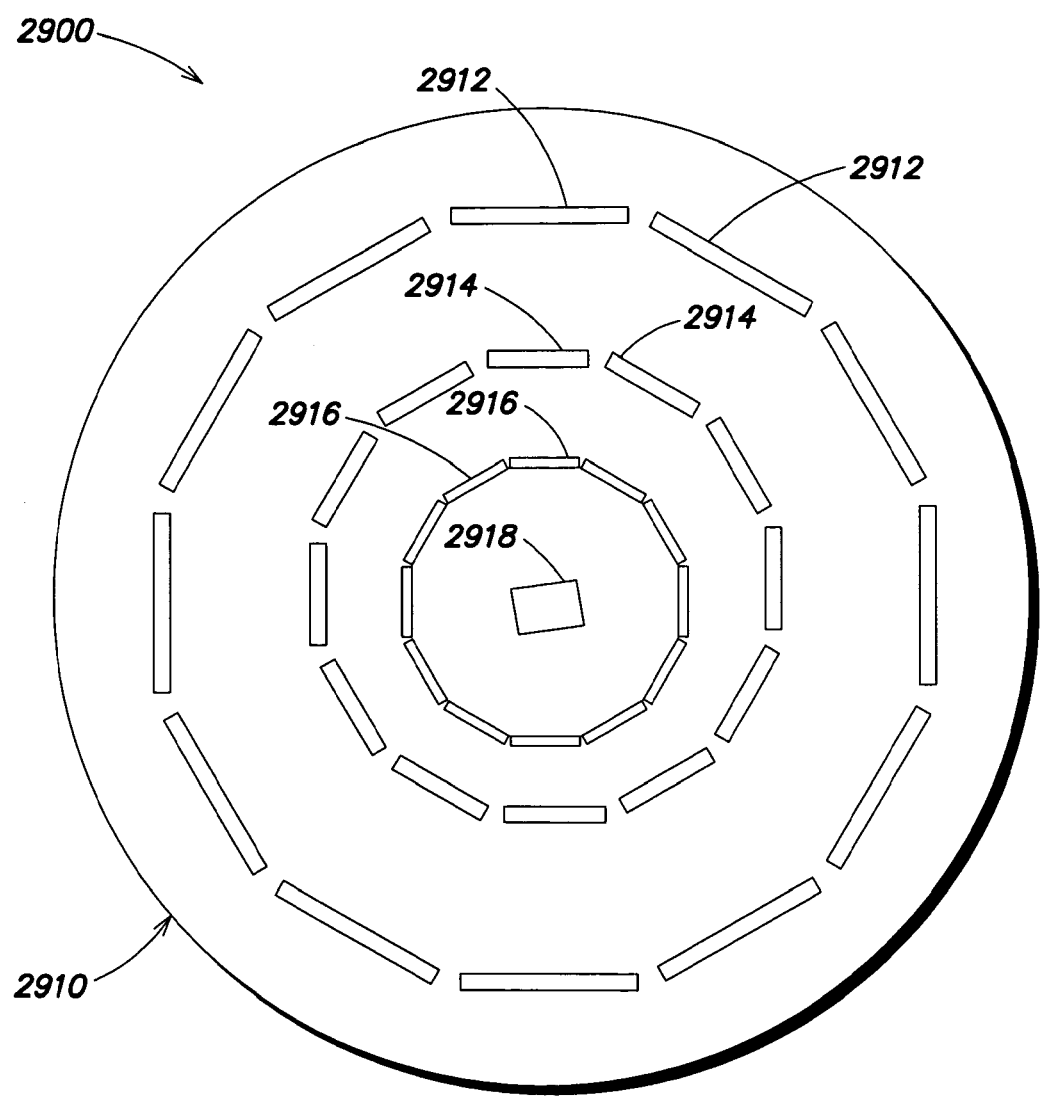
FIG. 29 is a schematic diagram illustrating an electrode array of an EIM probe associated with a sensor, in accordance with some embodiments of the invention.

FIG. 29 illustrates schematically an EIM probe which allows obtaining measurements in addition to impedance measurements, in accordance with some embodiments of the invention. In this example, an electrode array 2900 of the EIM probe is illustrated, which may be mounted on a suitable base 2910. Base 2910 may be positioned on a head of the EIM probe.

As shown in FIG. 29, electrode array 2900 may comprise a plurality of current-injecting electrodes 2912 arranged in an outer ring and a plurality of voltage-measuring electrodes 2914 and 2916 arranged in two respective inner rings. Any suitable number of electrodes may form each of the rings, with different rings having the same or different number of electrodes. The electrodes may be of any suitable size and shape and may be manufactured from any suitable material.

It should be appreciated that electrode array 2900 may comprise any suitable number of rings dedicated to injecting current or measuring voltage. As discussed above, electrode array 2900 may be reconfigurable. Thus, different combinations of excitation and pickup electrodes may be selected so that the electrodes are applied to a region of a tissue of a patient at multiple different orientations with respect to a direction of the muscle fibers. The different combinations of the electrodes may be selected during EIM measurements or at any other suitable time.

An EIM measurement system in accordance with some embodiments of the invention may obtain, in addition to impedance measurements of a region of tissue using an EIM probe, measurements of other different characteristics of the region of tissue. These characteristics may include, for example, a temperature of the skin, moisture content of the skin and any other suitable characteristics. Also, ultrasound, electrical tomography and other measurements may be performed at a region of tissue to which the EIM probe is applied. Furthermore, in some embodiments, a degree of pressure with which the EIM probe is applied to a region of tissue may be measured. The EIM measurements may be adjusted based on values indicative of different characteristics of the tissue obtained from the additional measurements.

FIG. 29 illustrates that a suitable sensor 2918 may be placed in proximity to electrode array 2900. In this example, the sensor is shown to be placed at a center of electrode array 2900. Though, it should be appreciated that embodiments of the invention are not limited in this respect and the sensor may be placed at any suitable location. The sensor may be, for example, at least one temperature sensor, at least one pressure sensor, at least one moisture sensor, or at least one ultrasound sensor. It should be appreciated that, even though one sensor 2918 is shown in FIG. 29, more than one sensor may be placed at suitable locations within the electrode array. For example, to monitor pressure with which the ELM probe is applied to a region of tissue, multiple pressure sensors may be placed at more than one location within the electrode array.

Any suitable respective device may be used as each of the sensors. Moreover, the sensors may be associated with the EIM probe in any suitable manner. For example, one or more sensors may be incorporated at a head of the EIM probe.

In some embodiments, the EIM measurements may be supplemented with electrical impedance tomography measurements collected by any suitable device. For example, electrodes of the electrode array, in any suitable configuration, may be used to perform the electrical impedance tomography measurements.

In some embodiments, the EIM measurement system may detect a degree of contact of each electrode of the electrode array 2900 with the surface of the skin in a region of tissue to which the EIM probe is being applied. The degree of contact may be detected in any suitable manner. For example, strength of the signal collected as a result of application of current via excitation electrodes may be used as an indication of the degree of contact.

In some embodiments, the electrode array of the EIM probe may comprise two or more sets of electrodes, where each set comprises excitation and pickup electrodes and the sets may simultaneously be used to determine muscle conditions at more than one location. As such, conditions of muscles at different depths beneath the skin surface may be assessed. Electrodes of different shapes and sizes, as well as forming different configurations (e.g., rings of different radii) may be used in the sets.

Figure 30:
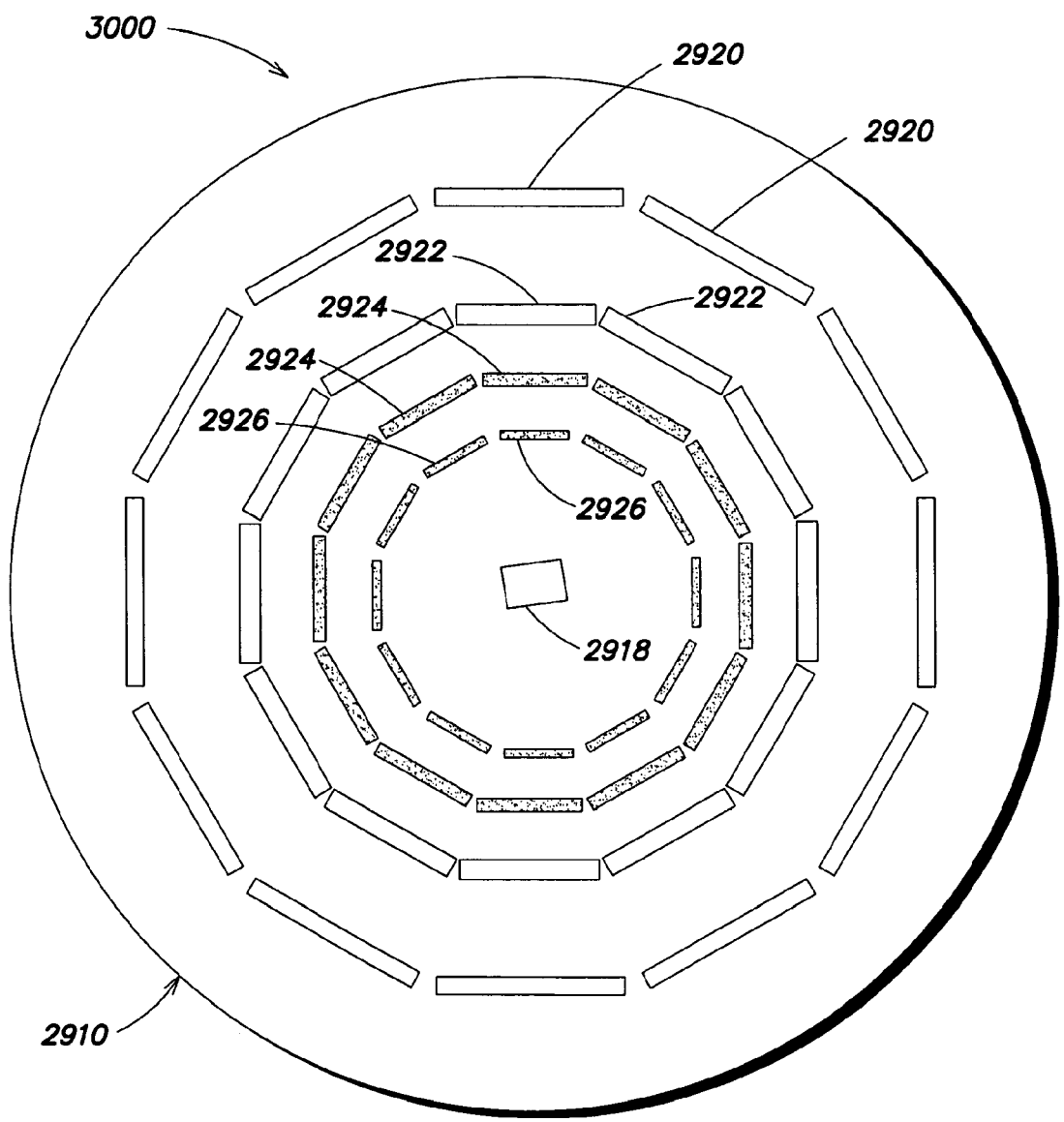
FIG. 30 is a schematic diagram illustrating an electrode array comprising two sets each including excitation and pickup electrodes, in accordance with some embodiments of the invention.
Figure 31A:
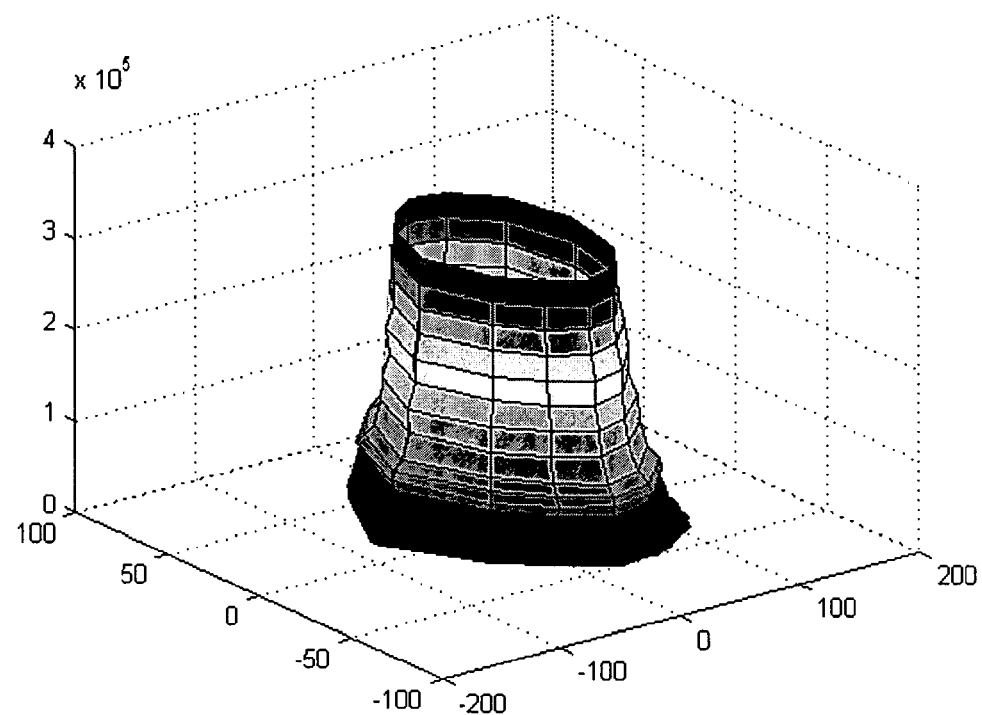
FIG. 31 illustrates four cylindrical plots generated based on results of EIM measurements conducted on a healthy patient (plots A and B) and a patient with amyotrophic lateral sclerosis (ALS)
Figure 31B:
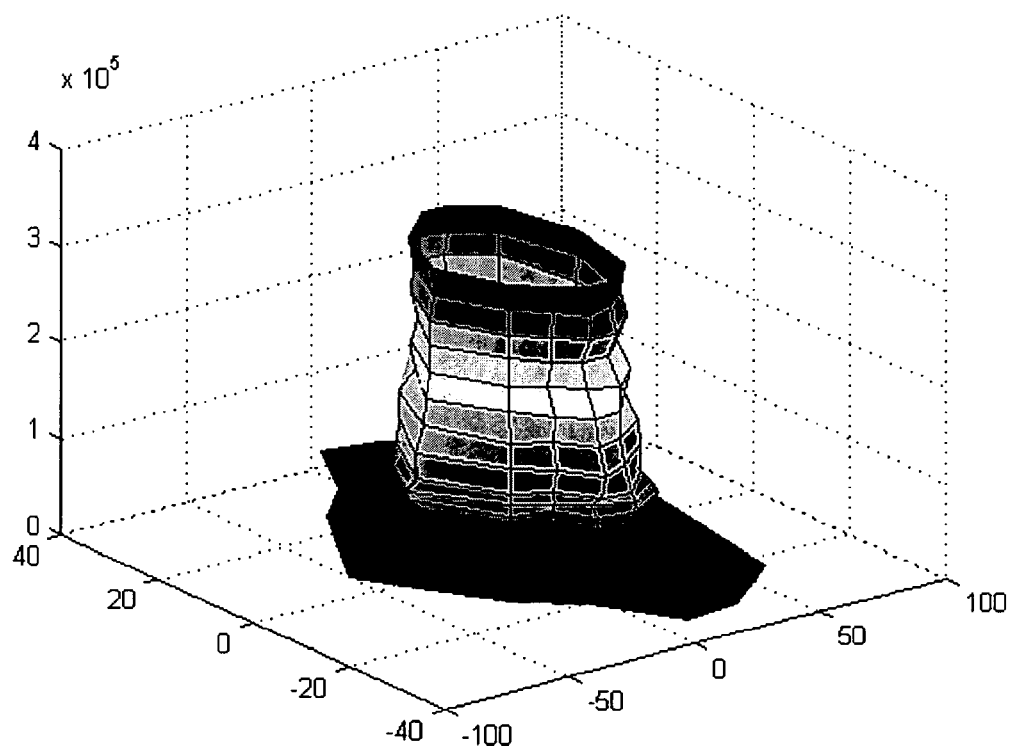
Figure 31C:
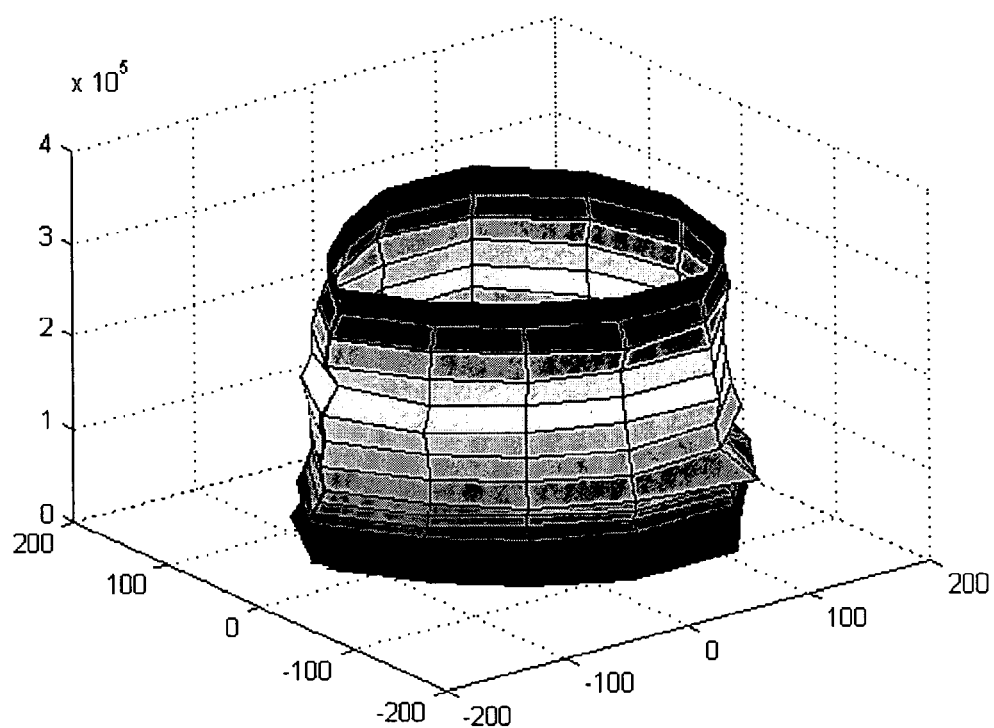
Figure 31D:
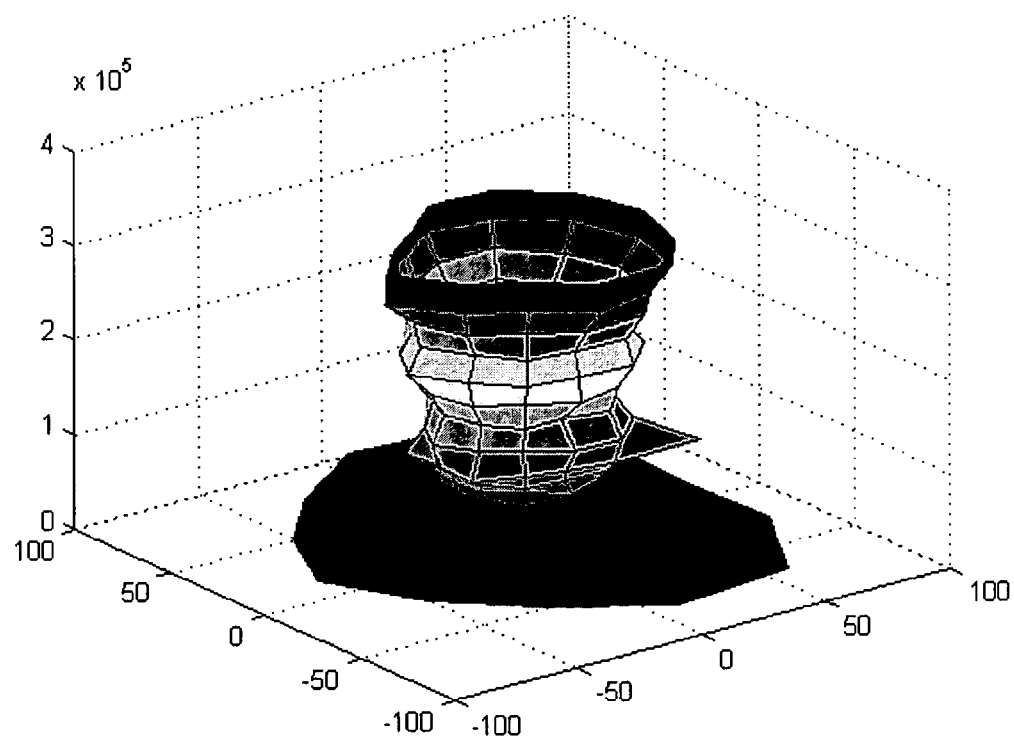
Figure 32A:
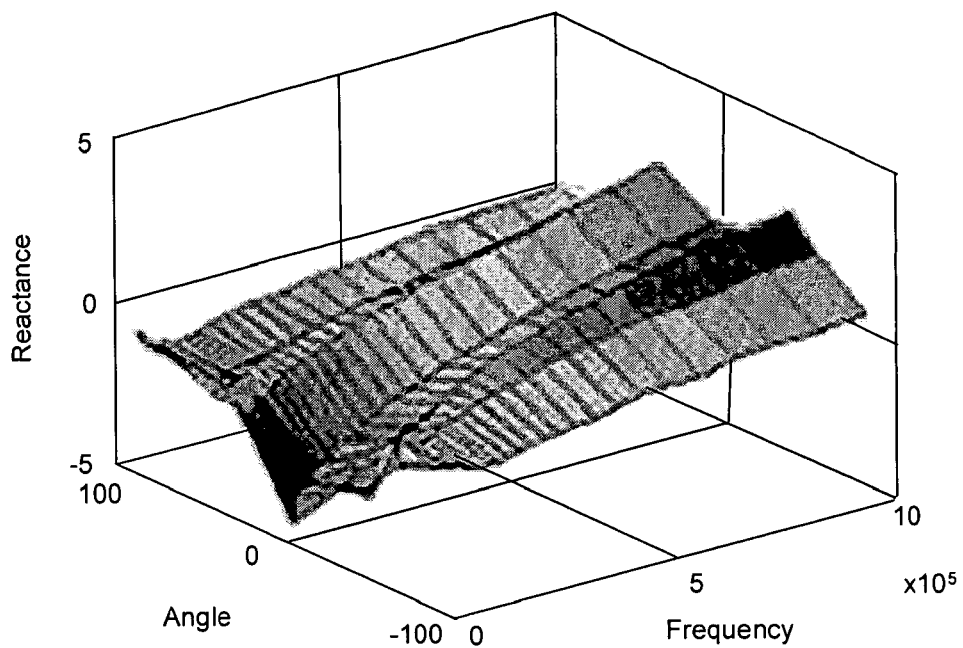
FIG. 32 illustrates results of difference between EIM measurements on contracted and relaxed healthy tibialis anterior muscle and contracted and relaxed tibialis anterior muscle affected by a radiculopathy.
Figure 32B:
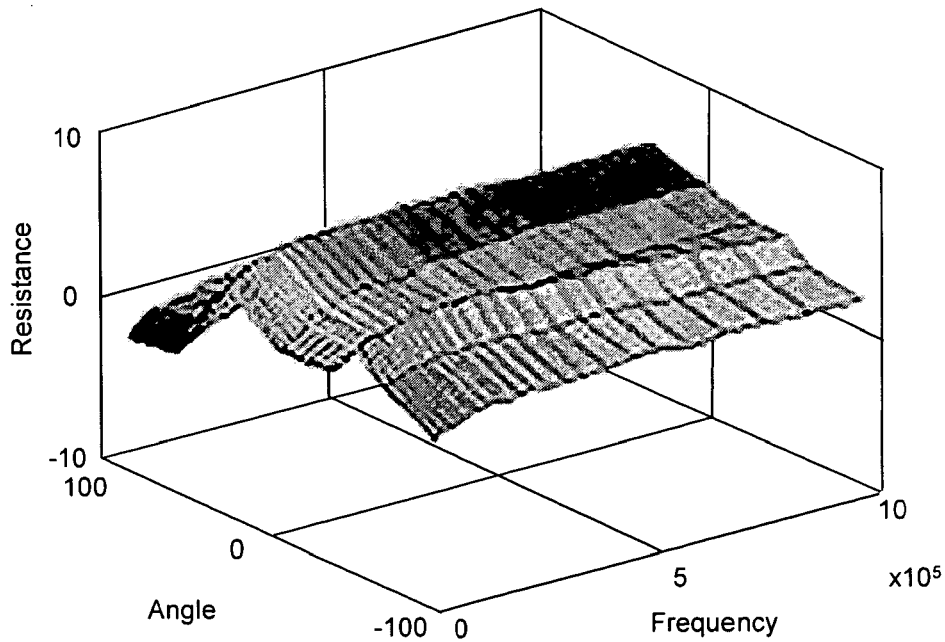
Figure 32C:
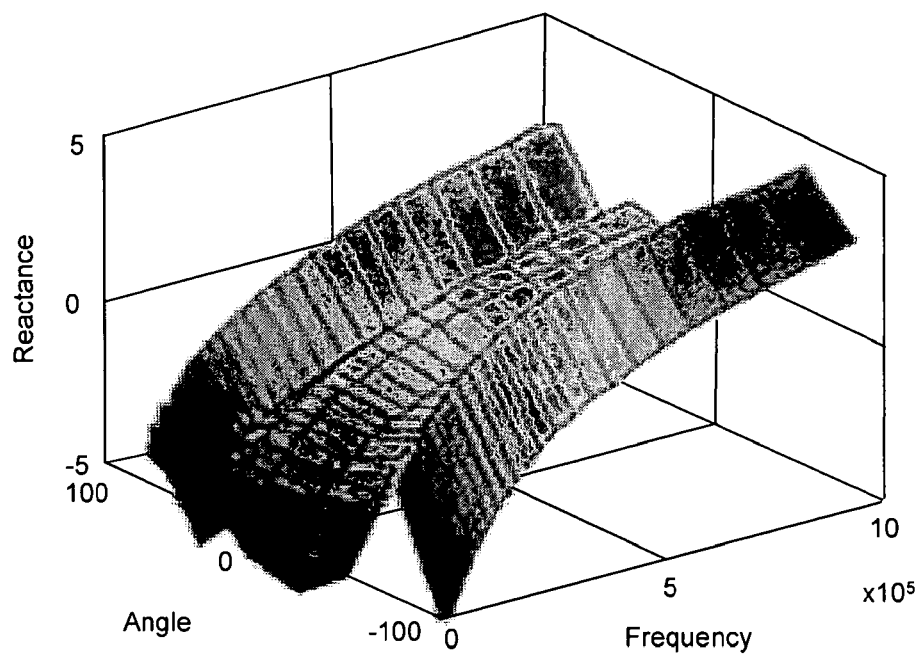
Figure 32D:
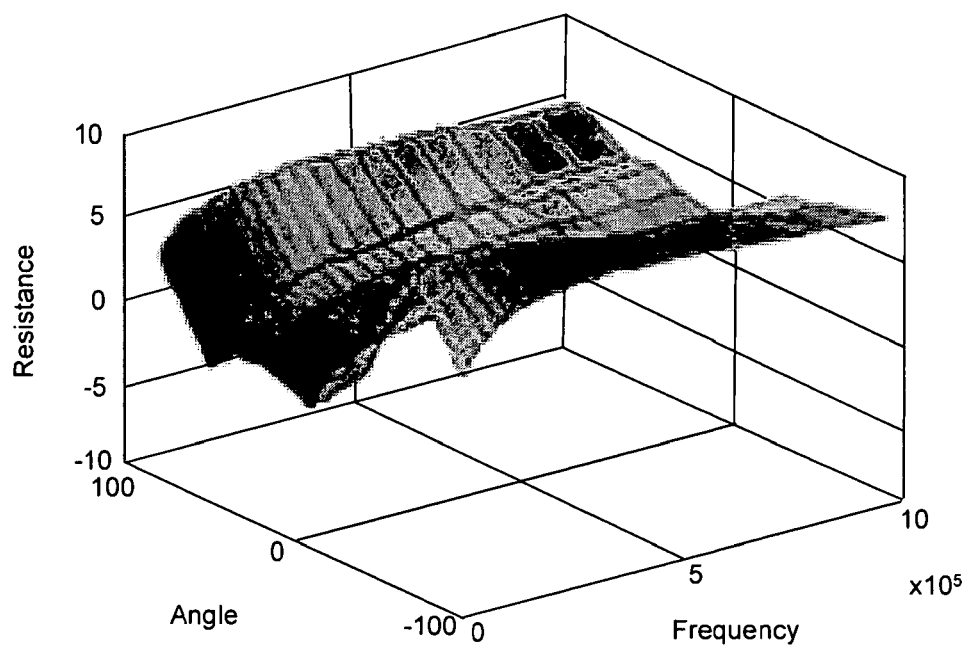

FIG. 30 illustrates schematically an example of an electrode array 3000, which may be located on base 2910 and may include, similarly to electrode array 2900, one or more sensors 2918. In this example, electrodes 2920 forming the outermost ring may be excitation electrodes and electrodes 2922 forming a ring within the outermost ring may be pickup electrodes. Electrodes 2920 and 2922 may be used to detect conditions of muscles at larger depths underneath the skin surface. Distortions in the results of the measurements due to skin-subcutaneous fat may be accounted for. In a similar manner, electrodes 2924 forming a ring within electrodes 2922 may be excitation electrodes and electrodes 2926 forming the innermost ring may be pickup electrodes. Electrodes 2924 and 2926, shown for the clarity of the presentation in grey shade, may be used to detect conditions of muscles at smaller depths underneath the skin surface. Distortions in the results of the measurements due to skin-subcutaneous fat may be accounted for.

In some embodiments, different data analysis techniques may be utilized to analyze results of impedance measurements and measurements of other parameters obtained using the EIM system described herein. Regardless of how data on a region of tissue is obtained, the data may be analyzed in any suitable way. For example, different three-dimensional and other plots may be generated for assessment of muscle condition. Also, results of EIM measurements may be combined in a suitable manner with results of additional measurements (e.g., measurements obtained using sensors). Results obtained for a healthy muscle may be compared to results of measurements obtained from a region of interest. Also, results obtained for a relatively healthy muscle within the same patient (e.g., on the opposite side or at a proximal location as compared to a distal location on the same patient) may be compared to the results of measurements obtained from the region of interest. Any other suitable measurements may be compared. Also, the EIM measurements and the measurements of other parameters may be compared to suitable respective values (e.g., thresholds).

Thus, three-dimensional plots demonstrating frequency-angle-impedance (i.e., resistance (R), reactance (X) and a phase ($\theta$)) may be generated for both disease diagnosis and assessment of disease progression over time. Also, cylindrical plots and any other suitable plots may be generated. Such plots may be used for qualitative assessment of muscle condition. Thus, a user such as a physician may visually detect distortions and difference between results obtained on healthy and diseased muscles. It may be detected that acute or subacute neurogenic disorders (i.e., nerve disorders) may increase and distort the normal anisotropy of the muscle while simultaneously altering the multi-frequency pattern, showing a small increase in reactance and phase at higher frequencies as compared to those for normal muscle. Other diseases, such as more chronic neurogenic disorders or primary disorders of muscle, may reduce the measured anisotropy and also cause a more prominent elevation in reactance and phase at higher frequencies. However, a variety of other possible combinations of changes may also occur.

In some embodiments, as shown in FIGS. 26-28, the EIM measurements may be analyzed to detect that anisotropy of the muscle may be elevated when the muscle is affected by a neurogenic disease and may be reduced when the muscle is affected by a myopathic disease. Furthermore, the EIM measurements may be used to detect a change in a dependency of characteristics of muscle tissue obtained using the EIM measurement system on the frequency of the applied signal, where the change may be indicative of an abnormal condition of the muscle tissue. The characteristics of muscle tissue may comprise resistance, reactance and any other suitable characteristic.

FIG. 31 illustrates, as an example, four cylindrical plots generated based on results of EIM measurements conducted on biceps of a healthy patient (plots A and B) and on biceps of a patient with ALS (plots C and D). Plots A and C illustrate resistance and plots B and D illustrate reactance. FIG. 31 shows that both resistance plot C and reactance plot D for the ALS patient exhibit distortion as compared to resistance plot A and reactance plot B for the healthy patient. Accordingly, identifying a distortion in plots generated on EIM measurements as compared to analysis of similar values for a healthy patient may be used as an indication of changes in the muscle. The degree of the changes may be determined based on a degree and a specific pattern of the distortion.

As discussed above, EIM measurements may be conducted on relaxed and contracted muscle of a patient. FIG. 32 illustrates results of EIM measurements for a patient with radiculopathy of the right side. The EIM measurements on both tibialis anterior muscles are illustrated. The difference in reactance (plots A and C) and resistance (plots B and D) between measurements on relaxed and contracted muscle is plotted. Plots A and B show the difference between the relaxed and contracted states of healthy tibialis anterior muscle and plots B and C show the difference between the relaxed and contracted states of tibialis anterior muscle affected by radiculopathy. As shown in FIG. 32, clear differences may be observed between the respective differences in measurements on relaxed and contracted muscle of a healthy and diseased muscle. Accordingly, assessing the difference between EIM measurements on relaxed and contracted states of healthy and diseased muscles, respectively, may help identify changes in muscle conditions.

In some embodiments, more complex algorithms may be utilized to accurately diagnose a disease or an abnormal condition, measure disease progression or improvement or a type of a disease present. Such algorithms may use a combination of factors, including the multi-frequency, multi-angular measurements with contraction and correction for temperature and pressure as well as skin-subcutaneous fat thickness (obtained using the multiple concentric rings described above, via ultrasound measurements, or using any other suitable techniques).

In some embodiments, the three-dimensional plots generated from impedance measurements obtained using the EIM probe may be used to derive into simple scores can be developed that would allow for rapid assessment of whether a condition is worsening, stabilizing, or improving over time or to assist with specific disease analysis. Once derived, such "EIM scores" may provide convenient measures of a disease type and a disease status.

The EIM measurement system using the EIM probe in accordance with some embodiments of the invention may be used to obtain impedance measurements of a region of tissue for any suitable purposes that are not limited to detection and diagnosis of a disease. Because the EIM measurement system described herein may help to detect changes in a structure of the underlying muscle, the system may be useful in a variety of different applications. The data analysis techniques described above may be used to demonstrate distortions in the impedance measurements indicative of the changes in the muscle. Any other suitable data analysis techniques may be used as well.

As one of applications of the EIM measurement system, the impedance measurements may be employed to assess improvement in muscle condition (e.g., due to exercises) beyond a certain point, which may be referred to as a baseline. This may be used by professional athletes or any other people involved in physical training whose muscle condition may be monitored to track and assess progress of the training. In such situations, EIM measurements may be conducted on contracted and relaxed muscles. Also, the EIM measurements may be used for assessment of muscle conditions indicative of potential muscle overuse injury and other disorders.

The EIM measurements using the EIM probe in accordance with some embodiments of the invention may also be used to assess changes in muscle caused by disuse of the muscle which may happen because of an orthopedic or other injury, weightlessness (e.g., due to a prolonged exposure to microgravity) and other conditions. Also, stages of recovery from these conditions may be tracked and assessed. Also, the EIM probe may be used to monitor and adjust a course of rehabilitation after injury or after surgery (e.g. joint replacement).

Further, the EIM probe may be used to detect muscle injury caused by trauma and/or bleeding. Also, because metallic (e.g., shrapnel) and non-metallic objects embedded in skin, subcutaneous fat or muscle may distort the impedance measurements, such discrete objects may be localized using the EIM measurements. The electrode array of the EIM probe may need to be reconfigured for such detection.

As another application for the EIM measurement system, "sarcopenia" or muscle atrophy and weakness due to aging and other factors (e.g., lack of physical activity) may be detected. Sarcopenia presents one of the major health concern in Western societies in which life expectancy has increased. Pharmaceutical companies undertake large efforts to develop drugs to inhibit or reverse the effects of sarcopenia. The impedance measurements and their analysis may be employed to detect and monitor different degrees of sarcopenia present and may help direct efforts for treating this condition, including developing a therapy.

The EIM probe may be used to assess muscle condition not only in humans but may also be employed for various veterinary uses. Assessing muscle condition using this non-invasive technique may be useful in animals, especially race horses and dogs. Muscle conditions of cattle raised for food may also be evaluated. The EIM probe may be adapted to be applied to a region on tissue in an animal—for example, electrodes of the electrode array may be modified to allow the probe to penetrate through the fur or hair. Also, other modification to the EIM probe may be made to make the probe suitable for veterinary uses.

In addition, the EIM probe may be used to assess quality of food, such as various types of meat.

Having thus described some illustrative embodiments of the invention, it should be apparent to those skilled in the art that the foregoing is merely illustrative and not limiting, having been presented by way of example only. Numerous modifications and other illustrative embodiments are within the scope of one of ordinary skill in the art and are contemplated as falling within the scope of the invention. In particular, although many of the examples presented herein involve specific combinations of method steps, system element, instrument elements and/or probe elements, it should be understood that those acts and those elements may be combined in other ways to accomplish the same objectives. Acts, elements and features discussed only in connection with one embodiment are not intended to be excluded from a similar role in other embodiments.

What is claimed is:

1. A system for determining muscle condition of a region of muscle tissue, the system comprising:
 a portable probe comprising:
  a body comprising a head bearing a base;
  a plurality of electrodes mounted on the base;
 a control component configured to detachably couple to the portable probe, the control component configured to:
  provide a first electrical signal comprising a plurality of frequencies to at least one first subset of a first plurality of electrodes to apply the first electrical signal to the region of tissue; and
  detect a second electrical signal from at least one second subset of a second plurality of electrodes at the region of tissue resulting from the application of the first electrical signal at the first subset of the first plurality of electrodes;
  reconfigure the first plurality of electrodes to select at least one third subset of the first plurality of electrodes to apply the first electrical signal to the region of tissue; and
  reconfigure the second plurality of electrodes to select at least one fourth subset of the second plurality of electrodes to detect the second electrical signal at the region of tissue resulting from the application of first electrical signal to the third subset of the first plurality of electrodes; and
 at least one temperature sensor, at least one moisture sensor, at least one pressure sensor, or at least one electrical tomography sensor configured to detect at least one first value of at least one characteristic of the region of tissue during a time when the first electrical signal is applied to the region of tissue;
 wherein reconfiguring of the first and second plurality of electrodes to select the at least one third subset and the at least one fourth subset is in response to receiving an indication to exclude at least one electrode from the at least first or second subset of electrodes based on the at least one first value.

2. The system of claim 1, further comprising an analysis component configured to analyze the second electrical signal to determine at least one second value indicative of the muscle condition of the region of tissue and to adjust the at least one second value based on the at least one first value, wherein the adjusted at least one second value is indicative of the muscle condition.

3. The system of claim 1, wherein the at least one sensor is embedded in proximity to the plurality of electrodes.

4. The system of claim 1, wherein the plurality of electrodes are detachably attached to the base via a locking mechanism, and wherein the system comprises a release mechanism for detaching the plurality of electrodes from the base.

5. The system of claim 1, further comprising an ultrasound measurement device.

6. The system of claim 1, wherein the head of the portable probe is shaped to conform to a curve and shape of a limb.

7. The system of claim 1, wherein the control component is further configured to control reconfiguring of at least one of the first plurality of electrodes and the second plurality of electrodes based on the at least one first value of at least one characteristic.

8. The system of claim 7, wherein the control component is further configured to control the reconfiguring of at least one of the first plurality of electrodes and the second plurality of electrodes automatically, in response to detection of the at least one first value of at least one characteristic.

9. The system of claim 1, wherein the at least one first value is used to adjust the first electrical signal during detection of the second electrical signal by the at least one second subset of the second plurality of electrodes.

10. The system of claim 1, wherein the at least one first value is used to select the at least one fourth subset of the second plurality of electrodes such that an electrode of the at least one second subset is excluded from the at least one fourth subset.

* * * * *